United States Patent [19]
Petersen et al.

[11] Patent Number: 6,015,882
[45] Date of Patent: Jan. 18, 2000

[54] **VACCINES, ANTIBODIES, PROTEINS, GLYCOPROTEINS, DNAS AND RNAS FOR PROPHYLAXIS AND TREATMENT OF *CRYPTOSPORIDIUM PARVUM* INFECTIONS**

[75] Inventors: Carolyn Petersen, Berkeley; James Leech, Daly City; Richard C. Nelson, San Francisco; Jiri Gut, Novato, all of Calif.

[73] Assignee: The Regents of the University of California

[21] Appl. No.: 08/700,651

[22] Filed: Aug. 14, 1996

Related U.S. Application Data

[63] Continuation-in-part of application No. 08/415,751, Apr. 3, 1995, Pat. No. 5,643,772, which is a continuation of application No. 08/071,880, Jun. 1, 1993, abandoned, which is a continuation-in-part of application No. 07/891,301, May 29, 1992, abandoned.

[51] Int. Cl.[7] .................................................. C07K 1/00
[52] U.S. Cl. ................... 530/350; 435/172.3; 424/191.1
[58] Field of Search ...................... 435/172.3; 424/191.1; 514/311

[56] References Cited

U.S. PATENT DOCUMENTS

| | | | |
|---|---|---|---|
| 5,318,979 | 6/1994 | Davis | 514/311 |
| 5,591,434 | 1/1997 | Jenkins et al. | 424/191.1 |
| 5,643,772 | 7/1997 | Petersen et al. | 435/172.3 |

OTHER PUBLICATIONS

Nina et al, Infect. Immunity, Apr. 1992, vol. 60(4), p 1509–1513.
Uhl et al, Infect. Immunity, Apr. 1992, vol. 60(4), p 1703–1706.
Bjorneby et al, J. Immunol., vol. 145(1), 1990 p 298–304.
Riggs et al, J. Immunol, vol. 43(4), Aug. 1989, p 1340–1345.
Petersen et al, Infect. Imunity, Dec. 1992, vol. 60(12), p 5132–8.
Petersen et al, Infect. Immunity, Jun. 1992 vol. 60(6), p 2343–2348.
Peters, et al, Infect. Immunity, Jun. 1992, vol. 60(6), p 2309–2316.
Bonnin et al., Infect. Immun., May 1991, vol. 59(5), p 1703–1708.
Ortega Mora et al, Infect. Immun. 1992, vol. 60(8), pp. 3442–3445.

*Primary Examiner*—James C. Housel
*Assistant Examiner*—Ginny Allen Portner
*Attorney, Agent, or Firm*—Hana Verny

[57] ABSTRACT

Vaccines, antibodies, proteins, glycoproteins, DNAs and RNAs useful for passive or active prophylaxis and treatment of Cryptosporidium infections. Cryptosporidium antigen comprised of a protein with or without carbohydrates attached thereto. Polyclonal and monoclonal antibodies directed against the antigen. DNA and RNA encoding the Cryptosporidium antigen, mutants, variants and fragments thereof.

17 Claims, 10 Drawing Sheets

MAb=Monoclonal 10C6 antibodies

PolyAb=Polyclonal anti-GP900 antibodies

CO=Sporozoite surface protein control

MAb=Monoclonal 10C6 antibodies

PolyAb=Polyclonal anti-GP900 antibodies

SHED BP900         BP900

VACCINES, ANTIBODIES, PROTEINS, GLYCOPROTEINS, DNAS AND RNAS FOR PROPHYLAXIS AND TREATMENT OF *CRYPTOSPORIDIUM PARVUM* INFECTIONS

This application is a continuation-in-part of the U.S. application Ser. No. 08/415,751 now U.S. Pat. 5,643,772 filed on Apr. 3, 1995 which is a continuation of Ser. No. 08/071,880 filed on Jun. 1, 1993, now abandoned which is a continuation-in-part of Ser. No. 07/891,301 filed May 29, 1992, now abandoned.

This invention was developed partially with U.S. Government support under National Institutes of Health Grant Nos. AI-29882 and AI 30295. The U.S. Government may have certain rights in this invention.

BACKGROUND OF THE INVENTION

1. Field of the Invention

This invention concerns vaccines, antibodies, proteins, glycoproteins, DNAs and RNAs for prophylaxis and treatment of Cryptosporidium or Cryptosporidium infections. In particular, this invention concerns a Cryptosporidium antigen comprised of a protein with or without carbohydrates attached thereto, as well as polyclonal and monoclonal antibodies directed against the antigen. Additionally, the invention concerns DNA and RNA encoding the Cryptosporidium antigen, mutants, variants and fragments thereof.

2. Background and Related Disclosures

The genus Cryptosporidium consists of Apicomplexan parasites that invade and develop within epithelial cells of the gastrointestinal, hepatobiliary and respiratory tracts of a wide variety of vertebrates including reptiles, birds and mammals. Cryptosporidium was recognized as a cause of animal disease for several decades before the first cases of human cryptosporidiosis were reported in 1976. However, it was not until 1982 that the magnitude of the disease caused by this parasite in both AIDS patients and immunocompetent hosts began to be appreciated. Subsequently, Cryptosporidium has been found to be among the top four causes of human diarrhea worldwide, and to be an increasingly recognized cause of diarrhea in children, animal care workers, and travelers. (*Cryptosporidium in Humans*, Ed. J. P. Dubai et al., CRC Press, Boca Raton (1990)).

Large waterborne outbreaks of cryptosporidiosis caused by contaminated municipal water supplies in the U.S. and in the UK have been noted in the last ten years (*N. Engl. J. Med.*, 320:1372 (1989), and 33:161 (1994)). The most recent outbreak in Milwaukee in April 1993 involved 400,000 persons and led to the subsequent deaths of more than 100 immunocompromised persons. Like a number of other waterborne outbreaks, the Milwaukee outbreak appears to have been due to contamination from farm or abattoir run-off and specifically due to cryptosporidiosis among cows/calves. Nosocomial transmission in hospitals from patients to staff, patient to patient, and contaminated ice to patients and staff have also been well documented (*J. Inf. Dis.*, 158:647 (1985)).

Waterborne and nosocomial spread reveal a number of biological characteristics of oocysts. First, the infectious dose of the parasite is very low. The $ID_{50}$ for human volunteers with normal immune systems is 132 oocysts (*New Engl. J. Med.*, 332:855 (1995)). Second, infected hosts, for example calves, excrete large numbers of oocysts; on the order of $10^{10}$/day. Third, the oocysts are fully sporulated and ready to infect when excreted. Fourth, the oocysts are environmentally hardy; they remain infectious in cool, moist areas for 3–4 months, and they are not killed by chlorine levels permissible in drinking water. Fifth, the oocysts are quite small, 4–6 $\mu$m, and are thus difficult to filter.

The clinical importance of cryptosporidiosis has increased markedly with the recognition of a life-threatening form of the disease in patients with immunodeficiency disorders such as AIDS, hypogammaglobulinemia, and chemotherapeutic immunosuppression. The prevalence of cryptosporidiosis in AIDS patients in the U.S. is estimated to be 5–10% and in central Africa 40%. Immunodeficient patients may have fulminant cryptosporidial diarrhea that may persist until death, whereas the diarrhea of immunocompetent patients is self-limited and rarely lasts more than 2–4 weeks. Cholera-like diarrhea is common in immunocompromised patients with reported losses of up to 17 liters of water per day. Hepatobiliary disease may result in severe abdominal pain and nausea. Removal of immunosuppression in chemotherapy patients leads to resolution of the diarrhea. Occasionally, AIDS patients with cryptosporidiosis will be able to eliminate the parasite after initiation of anti-retroviral therapy (*Am. Intern. Med.*, 116:840 (1992)).

Among those who develop the disease, a quarter have CD4 counts greater than 209, suggesting that the cryptosporidiosis disease may appear relatively early in the course of HIV disease. Unfortunately, few details about the biology of the organisms and the molecular mediators of the disease process have been described and no effective therapy has been discovered.

The infective forms of Cryptosporidium, called sporozoites and merozoites, adhere to the host cell and release the contents of anterior organelles (rhoptries, micronemes or dense granules) during the invasion process (*Parasitol. Today*, 8:28(1992)). Proteins involved in these events have in many instances been found to be the target of invasion blocking immunity in vitro and neutralization in vivo (ibid). Active and passive immunization studies using malaria and Toxoplasma challenged or infected hosts, have shown that certain secreted components of the apical complex organelles are the target of protective antibodies in these related Apicomplexan parasites. In some cases, as for example in the case of the circumsporozoite and merozoite surface proteins of malaria, these antigens are under development as vaccines.

While the actual interaction between Cryptosporidium and the host's immune system is poorly understood, it is known that disruption of either the cellular or the humoral components can result in protracted cryptosporidiosis (*Parasitol. Today*, 8:24 (1992)). However, specific antibodies alone neutralize the organism's infectivity. In vitro and in vivo observations indicate that antibodies to *Cryptosporidium parvum* inhibit invasion and intracellular development leading to protection in challenge experiments, or amelioration of infection in established disease (*Infect. Immun.*, 59:1172 (1991)).

One source of such antibodies is hyperimmune bovine colostrum (HBC) collected from cows immunized with Cryptosporidium oocysts. Calves challenged with Cryptosporidium oocysts are protected from the development of the disease by the administration of HBC (*Infect. Immun.*, 61:4079 (1993)). Some immunocompromised AIDS patients infected with Cryptosporidium have also responded to HBC with a reduction in, or disappearance of, the symptoms of the disease (*Gastroenterology*, 98:486 (1990)). Immunoglobulin from HBC (HBC Ig) has been found to inhibit the ability of the sporozoite to invade and/or develop intracellularly in vitro and it has been used to immunoprecipitate at least 22 different surface radioiodinated proteins of Cryptosporidium sporozoites. Western blot analysis of proteins of whole oocysts, which contain sporozoites, indicates that HBC predominantly recognizes two proteins of sizes 250 kDa and >900 kDa (*Infect. Immun.*, 61:4079 (1993)).

The use of HBC for human use is problematic. HBC produced using whole oocysts is batch dependent and this may lead to the development of passive immune preparations which are not uniform in immunogenicity and potency. This generates a problem when these immune preparations are to be administered to human patients as such non-uniformity may result in failure of protection. In addition, it would be desirable to allow preparation of large amounts of antigen expressed in heterologous systems rather than to purify the oocyst.

Thus, there is a continuous need for immunogenic agents which are reasonably reproducible and have uniform and controllable immunogenicity and potency, which agents would be useful for the active and passive immunotherapy of cryptosporidiosis in both uncompromised and immunocompromised subjects, such as AIDS patients.

Additionally, there is a need to have available methods for reproducible expression of specific targets for Cryptosporidium antigens in large amounts, which antigens would provide a better immunogen. This approach requires that specific Cryptosporidium antigen genes are cloned and identified as potential candidates through their ability to elicit an antibody response that is immunoprotective. Before antibodies produced in this manner are tested in or administered to humans or animals, testing in in vitro assay of its inhibitory effect on invasion or intracellular development of the Cryptosporidium organism in cultured cells, and in vivo studies, would be desirable.

It is, therefore, a primary objective of this invention to provide polyclonal or monoclonal antibodies to be used for prophylaxis and treatment of cryptosporidiosis and to express a portion of the GP900 sequence/locus to provide target protein antigens allowing production of recombinant anti-Cryptosporidium vaccines and passive immune products.

All patents, patent applications and publications cited herein are hereby incorporated by reference.

SUMMARY OF THE INVENTION

One aspect of this invention concerns vaccines, antigens, antibodies, proteins, glycoproteins, DNAs and RNAs for prophylaxis and treatment of Cryptosporidium or Cryptosporidium infections.

Another aspect of this invention concerns a Cryptosporidium antigen comprised of an immunogenic protein without attached carbohydrates.

Another aspect of this invention concerns a Cryptosporidium antigen comprised of an immunogenic protein with attached carbohydrates.

Another aspect of this invention concerns polyclonal or monoclonal antibodies directed against the Cryptosporidium antigen.

Another aspect of this invention concerns DNA and RNA encoding or representing the Cryptosporidium antigen and fragments thereof.

Another aspect of this invention concerns polyclonal or monoclonal antibodies directed against invasive stages of cryptosporidial species capable of preventing and ameliorating the invasion of Cryptosporidium infection.

Another aspect of this invention concerns a synthetic or recombinant vaccine, useful for active immunization of animals and humans against Cryptosporidium infection.

Another aspect of this invention concerns a synthetic or recombinant protein useful for preparation of passive immune products for treatment of established infections.

Another aspect of this invention concerns a synthetic or recombinant DNA vaccine, capable of endogenous development of an inhibitory amount of anti-*Cryptosporidium parvum* antibodies.

Another aspect of this invention concerns a synthetic or recombinant RNA vaccine, capable of endogenous development of an inhibitory amount of anti-*Cryptosporidium parvum* antibodies.

Another aspect of this invention concerns an amino acid sequence (1721 aa) of a protein portion of GP900, a >900 kDa glycoprotein of sporozoites and merozoites, and its amino acid and size variants.

Another aspect of this invention concerns the DNA sequence of 5319 nucleotides encoding a protein portion of GP900, its nucleotide and size variants and its upstream (5') protein coding and regulatory elements.

Another aspect of this invention concerns the RNA sequence determined by the DNA sequence of GP900 and its nucleotide and size variants including the polyadenylation sequence.

Another aspect of this invention concerns an amino acid sequence (503 aa) of a protein portion of P68, a 50–100 kDa glycoprotein of sporozoites and merozoites, and its amino acid and size variants.

Another aspect of this invention concerns the DNA sequence of 2380 nucleotides encoding a protein portion of P68, its nucleotide and size variants and its upstream (5') protein coding and regulatory elements.

Another aspect of this invention concerns the RNA sequence determined by the DNA sequence of P68 and its nucleotide and size variants including the polyadenylation sequence.

Another aspect of this invention concerns the group of GP900 or P68 recombinant or expressed protein, or glycoprotein targets of antibodies which inhibit infection, invasion, or adhesion.

Another aspect of this invention concerns a method for prophylaxis and treatment of Cryptosporidium or Cryptosporidium infections using vaccines, antibodies, proteins, glycoproteins, DNAs and RNAs of the invention.

Another aspect of this invention concerns a method of prophylaxis, treatment, inhibition or retardation of a Cryptosporidium infection, comprising administering to a subject in need of such treatment an amount of anti-Cryptosporidium polyclonal or monoclonal antibodies, prophylactically or therapeutically effective, to provide immunity against infection or treatment for the disease.

Another aspect of this invention concerns a method of prophylaxis, treatment, retardation, or inhibition of Cryptosporidium infection, comprising administering to a subject in need of such treatment, a vaccine containing the polypeptide or glycoprotein of this invention or its DNA or RNA, capable of endogenous stimulation of the production of an inhibitory amount of anti-Cryptosporidium antibodies.

DEFINITIONS

Figure 1:
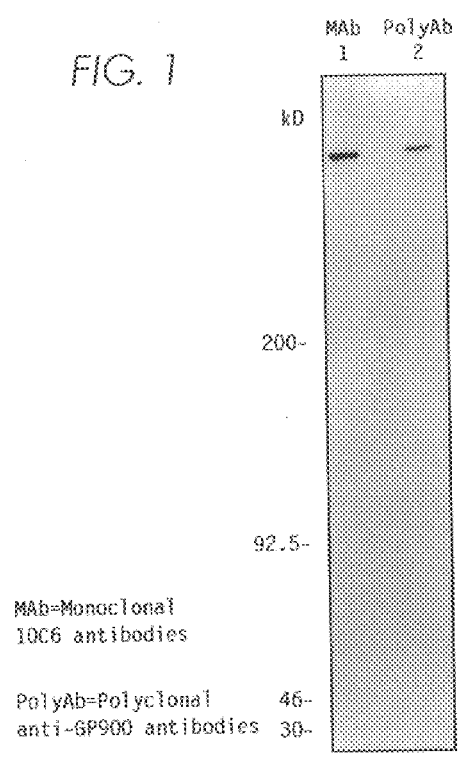
FIG. 1 is an immunoblot of *Cryptosporidium parvum* oocyst/sporozoite proteins showing detection of the >900 sporozoite protein with monoclonal and polyclonal antibodies to GP900.

As used herein:

"GP900" means a high molecular weight protein represented by 1721 amino acids and identified as SEQ ID NO: 5 of Mr greater than 900 kilodaltons (kDa) which may have an attached glycoprotein, said GP900 detected at the surface of sporozoites or merozoites. GP900 is the target of antibodies which inhibit infection, invasion or adhesion of Cryptosporidium.

"P68" means an apical protein of sporozoites or merozoites represented by 503 amino acids and identified as SEQ ID NO: 6 of Mr between approximately 50 and 100 kilodaltons which is a target of antibodies which inhibit infection, invasion or adhesion of Cryptosporidium.

The "structure" or "structural characteristics" of GP900 defines a protein, glycoprotein, DNA and RNA encoding the GP900 protein and includes all structural variations, mutations and fragments exhibiting the same function.

The "functionality" or "functional characteristics" of GP900 is defined by the interaction of antibodies to GP900 and structural variants described, such that the antibody inhibits infection, invasion or adhesion of Cryptosporidium.

"T-cell epitope" means targets which stimulate or elicit T cells or T cell mediated immune responses.

"Cell mediated immune responses" means responses stimulated or elicited by interaction of T cell epitope or T cell.

"The gene" or "genes encoding GP900" means DNA encoding a portion or all of the GP900 protein. One or more of these portions with or without carbohydrates attached include the targets of GP900 antibodies known as T-cell epitopes.

The "structure" or "structural characteristics" of P68 defines a protein, DNA and RNA encoding the P68 protein and includes all structural variations, mutations and fragments exhibiting the same function.

The "functionality" or "functional characteristics" of P68 is defined as the interaction of antibodies to P68 and structural variants described, such that the antibody inhibits infection, invasion or adhesion of Cryptosporidium.

"The gene" or "genes encoding P68" means DNA encoding a portion or all of the P68 protein. One or more of these portions include the targets of P68 antibodies known as T-cell epitopes.

"Sporozoites or merozoites" means any life stage which may invade host cells and any variant or mutant of said sporozoites or merozoites.

"Antibodies" means proteins which structurally interact with the target antigen and are produced when the antigen is introduced into an animal, such that they stimulate the immune system. The term also includes antibodies produced in vitro, such as antibodies produced by hybridoma cell cultures and chimeric proteins, as well as hybridoma cells and chimeric constructs introduced into the host to provide an in vivo antibody. "Antibodies to GP900" means proteins which structurally interact with the target antigen GP900 and inhibit infection, invasion or adhesion of the sporozoites or merozoites to the host cell.

"Antibodies to P68" means proteins which structurally interact with the target antigen P68 and inhibit infection, invasion or adhesion of the sporozoites or merozoites to the host cell.

"Monoclonal antibodies" means the monovalent antibodies produced by B cells fused to immortalized cells producing specific antibody to GP900 or P68.

"Polyclonal antibodies" means antibodies directed at GP900 or P68 which are not monovalent and are the products of multiple B cells in character.

"Carbohydrate" or "carbohydrate moiety" means any N- or O-linked carbohydrate or portion thereof, which is covalently linked to the protein of GP900 or P68.

"Target antigen" means protein or carbohydrate moiety attached to protein including variants defined by differential glycosylation and conformational change.

"Differential glycosylation" means glycoproteins which vary in the carbohydrate moieties attached to the protein backbone as a function of factors other than the sequence of the protein backbone.

"Conformational change" means change in the shape of the protein or the glycoprotein as a result of changes in the carbohydrate moieties bound to it and/or changes in the protein sequence.

"GP900 antigen" means a protein with or without a carbohydrate attached thereto which defines the capacity of Cryptosporidium sporozoites and merozoites to infect host cells.

"P68 antigen" means a protein with or without a carbohydrate attached thereto which defines the capacity of Cryptosporidium sporozoites and merozoites to infect host cells.

"GP900 DNA" means the sequence of 5319 nucleotides identified as SEQ ID NO.: 2 which encodes an amino acid portion of the protein sequence of GP900 protein (SEQ ID NO: 5) and any variant, 5' extension, mutation and fragment thereof, which corresponds to genes encoding the antigen.

"GP900 RNA" means the RNA sequence corresponding to 5164 bp of DNA sequence (SEQ ID NO. 1) which encodes the protein sequence of GP900 protein (SEQ ID NO: 5) and any 5' extension, variant, mutation and fragment thereof.

"P68 DNA" means the sequence of 1509 nucleotides identified as SEQ ID NO: 3 which encodes the protein sequence (SEQ ID NO: 6) of P68 protein and any 5' extension, variant, mutation and fragment thereof which corresponds to genes encoding the antigen.

"P68 RNA" means the RNA sequence corresponding to the 1509 nucleotides identified as SEQ ID NO: 2 which encodes the protein sequence of P68 protein (SEQ ID NO: 6) and any 5' extension, variant, mutation and fragment thereof.

"Vaccine" means a protein, recombinant protein, DNA or RNA from GP900 or P68 which upon introduction into a host, is able to provoke an immune response including but not limited to the production of antibodies, cytokines and other cellular responses.

"Prevention or prophylaxis" means the passive or active immunization with antibodies or vaccines of the invention such that disease or infection does not occur.

"Treatment" means therapeutic use of any protein, glycoprotein or antibody to inhibit existing infection in a host.

"Host" means a human or animal, including birds and cattle.

"Regulatory elements" means nucleotide sequences which control the expression of genes they regulate, typically by interaction with other macromolecular species such as proteins.

"Active immunity to infection" means the ability of an organism to produce specific responses such as production of cytokines, lymphokines, antibodies or other substances, or cellular capacity to inhibit or retard infection in response to a contact with an antigen.

"passive immunity to infection" means the transfer to a host of the specific antibodies or other substances or cells capable of inhibiting or retarding infection.

"Cryptosporidium species" means any organism belonging to the genus Cryptosporidium, such as, for example, *Cryptosporidium parvum* or Cryptosporidium muris, but also includes currently less well characterized other organisms such as, for example, Cyclospora and it is also meant to include apicomplexan parasites which invade the gastrointestinal tract, such as Eimeria. Cryptosporidium species comprise Apicomlexan parasites which primarily invade cells of the gastrointestinal tract and cause disease in a susceptible host.

"Recombinant vaccines" means 1) protein segments produced from recombinant DNA or RNA in vitro and then introduced in vivo; and 2) RNA or DNA introduced in vivo and capable of producing recombinant protein in situ. This term includes all vaccines other than those biologically derived.

"Biologically derived vaccines" means a protein or glycoprotein generated in the organism of origin.

"REA" means recombinant eluted antibodies.

DETAILED DESCRIPTION OF THE INVENTION

This invention relates to vaccines, antibodies, proteins, glycoproteins, DNAs and RNAs useful for prophylaxis and treatment of infections caused by any Cryptosporidium organism or any organism belonging to the Cryptosporidium species.

More specifically, the invention concerns: identification and isolation of Cryptosporidium antigens comprised of a protein or polypeptide with or without a carbohydrate attached thereto; identification of the DNA of the Cryptosporidium antigen gene within the locus; sequencing DNA encoding Cryptosporidium antigens; expressing portions of the locus encoding the Cryptosporidium antigens; and using the expressed antigens to prepare vaccines or polyclonal or monoclonal antibodies.

I. Cryptosporidium Antigens

Cryptosporidium organisms and particularly *Cryptosporidium parvum* are coccidian parasites of the gastrointestinal tract that cause a clinical syndrome of diarrhea for which there is currently no effective treatment. Infectivity of Cryptosporidium is mediated by a specific protein or polypeptide antigens of sporozoites or merozoites, the infective forms of Cryptosporidium.

Two antigen proteins, designated GP900 and P68 were identified. They were partially sequenced at the DNA level. The 3' sequence and 3' flanking regions for GP900 and P68 are documented. Two GP900 DNA sequences and two P68 DNA sequences were established. SEQ ID NO: 1 comprising 5164 bp encodes a portion of GP900. SEQ ID NO: 2 comprising 5319 bp encodes a portion of GP900 and includes the 3' flanking region. SEQ ID NO: 3 comprising 1509 b; encodes a portion of P68. SEQ ID NO: 4 comprising 2380 bp encodes a portion of P68 and includes 3' flanking region. The deduced partial sequences of encoded proteins GP900 (SEQ ID NO: 5) and P68 (SEQ ID NO: 6) were established.

The DNA encoding Cryptosporidium antigen can be coupled to Cryptosporidium DNA encoding regulatory elements located downstream or upstream or on another chromosome in the Cryptosporidium genome. These operably coupled DNA segments are able to bind selectively and specifically to Cryptosporidium molecules, such as proteins.

Expressed portions of the loci encoding GP900 and P68, are targets of polyclonal and monoclonal antibodies able to inhibit invasion/intracellular development in vitro and in vivo. The expression, identification and isolation of these recombinant proteins allows production of recombinant vaccines for active immunization of animals and humans against cryptosporidiosis as well as passive immune products for prevention and treatment of an established infection.

During the development of this invention, it has been shown and described in *Infect. Immun.*, 60:2343 (1992), 60:5132 (1992), and 61:4079 (1993), that a *Cryptosporidium parvum* expression library clone S34 encoded a portion of a protein larger than 900 kDa, recognized by hyperimmune bovine colostrum (HBC), which has been designated GP900.

The GP900 protein is highly abundant and is easily visualized by Coomassie blue staining of proteins on SDS-polyacrylamide gels (SDS-PAGE). Furthermore, it is known to be Triton X-100 soluble and N-glycosylated.

This protein has been localized at the anterior portion of the sporozoite and merozoite by immunofluorescence microscopy. Specifically, the protein has been detected in micronemes of these invasive stages by immunoelectronmicroscopy and has been shown to be accessible to surface radioiodination with $^{125}$I.

Monoclonal antibodies, which are specific for GP900, have been made according to Example 2. Three of six antibodies, namely 10C6, 7B3, and E6, made from a single fusion event in which the immunogen was an oocyst containing sporozoites, were specific to GP900, suggesting that GP900 is a highly immunogenic molecule of sporozoites. Three of eight antibodies, namely M2, M15 and M24 made from a second fusion event, in which the immunogen consisted of meronts, were also specific to GP900, suggesting that GP900 is a highly immunogenic molecule of merozoites.

The second Cryptosporidium antigen is a smaller protein identified as P68.

1. GP900 Protein, Glycoprotein, Recombinant Protein and DNA/RNA

A. Cryptosporidium Antigen Protein GP900

Cryptosporidium antigen GP900 is a high molecular weight glycoprotein of a Mr greater than 900 kilodaltons (kDa). The GP900 protein was detected in micronemes of developing merozoites and sporozoites. It is present on the surface of the sporozoites and is shed from the sporozoite surface in vivo in host cells. When deglycosylated, the GP900 core protein has a variable molecular weight of approximately 150–250 kDa. The GP900 protein has been identified as a target of anti-GP900 antibodies which inhibit Cryptosporidium infection, invasion or adhesion.

The GP900 protein sequence containing 1721 amino acids is seen in SEQ ID NO: 5. DNA encoding the GP900 protein contains 5164 base pairs and its sequence is depicted in SEQ ID NO: 1.

*Cryptosporidium parvum* was identified and isolated from oocysts of the Iowa and AUCP-1 isolates of *Cryptosporidium parvum* passaged through neonatal calves, as described in Example 1. Oocysts containing sporozoites were solubilized, resolved by SDS-PAGE and subjected to immunoblotting, according to *Infect. Immun.*, 60:5132 (1992). Proteins which are targets of an anti-oocyst/sporozoite antibody were visualized after incubation with the primary antibody by enzyme-linked immunosorbent assay (ELISA) or with $^{125}$I labeled Protein A followed by autoradiography.

Protective HBC Ig antibodies were, during the development of this invention, found to react predominantly with two proteins above 200 kDa in a Western blot of solubilized oocyst. The first protein had a size of 250 kDa. The second protein was >900 kDa and comigrated with GP900. In an attempt to determine whether the 250 kDa protein is a component of GP900, polyclonal antibodies against SDS solubilized GP900 were prepared.

Figure 2:
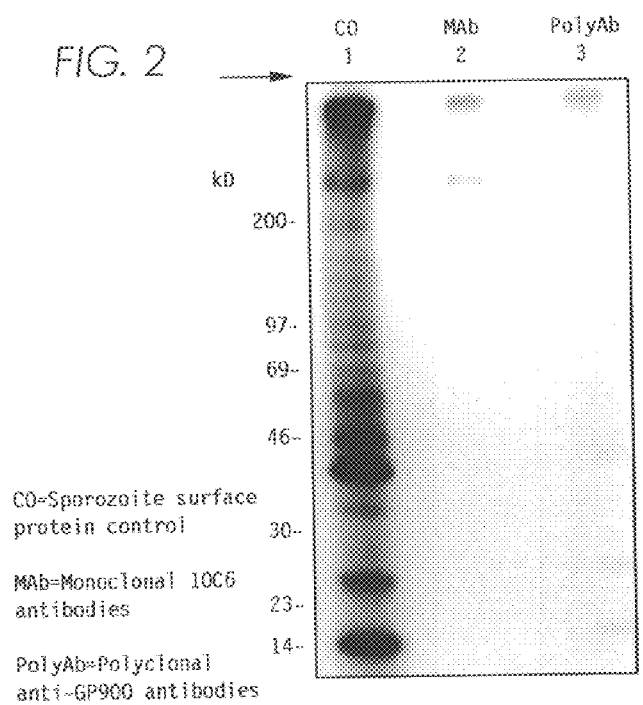
FIG. 2 is the immunoprecipitation of $^{125}$I surface label *Cryptosporidium parvum* sporozoite proteins using monoclonal and polyclonal antibodies to GP900.

Identification of the GP900 protein from the oocyst of Iowa and AUCP-1 isolates is illustrated in FIGS. 1 and 2.

Visualized Cryptosporidium antigen proteins were surface radioiodinated and immunoprecipitated using the method described in *Infect. Immun.*, 61:4079 (1993).

Triton X100 soluble GP900 of sporozoites was used to prepare polyclonal anti-GP900 antibody to clone the gene for GP900. To this end, the soluble fraction of GP900 was immunoprecipitated with monoclonal antibody (MAb) 10C6, and a >900 kDa molecular weight species was identified and excised, and used for immunization of mice for production of the anti-GP900 antibody. Polyclonal antibodies prepared against SDS solubilized GP900 and MAb 10C6, which were previously shown to detect GP900, were used to probe a Western blot, as seen in FIG. 1, and to immunoprecipate sporozoite surface labeled proteins, as seen in FIG. 2.

FIG. 1 shows a immunoblot of *Cryptosporidium parvum* oocyst/sporozoite proteins of the AUCP-1 isolate separated by SDS-PAGE. Lane 1 shows the MAb 10C6 culture supernatant. Lane 2 shows the polyclonal anti-GP900 in 1:5000 dilution.

As seen in FIG. 1, a single molecular species, GP900, was identified at ~900 kDa by both monoclonal and polyclonal antibodies. Cross-immunoprecipitation studies confirmed that the same, approximately 900 kDa size, protein was seen by both antibodies. At prolonged periods of detection, a less prominent ladder of bands between the 200 and 92 kDa markers was observed.

FIG. 2 shows immunoprecipitation of $^{125}$I radiolabeled *Cryptosporidium parvum* sporozoite surface proteins of the AUCP-1 isolate separated by 5–15% SDS-PAGE. Lane 1 shows radiolabeled *Cryptosporidium parvum* sporozoite surface protein control (10$^7$ sporozoites/lane). Lane 2 shows radiolabelled *Cryptosporidium parvum* sporozoite surface proteins immunoprecipitated with monoclonal MAb 10C6. Lane 3 shows radiolabelled *Cryptosporidium parvum* sporozoite surface proteins immunoprecipitated with polyclonal anti-GP900.

Immunoprecipitation of $^{125}$I labeled sporozoites with polyclonal anti-GP900 and monoclonal 10C6 antibodies revealed that polyclonal anti-GP900 only detects one protein, GP900, while monoclonal 10C6 additionally detects a protein of 250 kDa. These data suggest that MAb 10C6 detects a shared epitope on two surface accessible proteins, GP900 and a protein of Mr 250,000. However, the 250 kDa protein also could be a precursor or processed form of GP900 and as such is a part of the invention.

These results show that polyclonal anti-GP900 antibody is a more specific detection reagent for GP900 than monoclonal Ab10C6 by Western blot and by immunoprecipitation of surface proteins. This confirms that polyclonal anti-GP900 antibody is an appropriate antibody for GP900 localization experiments and for detection of clones in a Cryptosporidium expression library.

Prominent sporozoite surface proteins of other Apicomplexan parasites, for example, the circumsporozoite protein of the Plasmodium species, which contains the binding ligand for adhesion of the malaria sporozoite to its host cell, the hepatocyte, are known to be shed from the surface of sporozoites in vivo.

In order to determine whether GP900 similarly was shed from the surface of Cryptosporidium sporozoites, living sporozoites were allowed to glide on poly-L-lysine coated slides. Results are shown in FIG. 3.

Figure 3A:
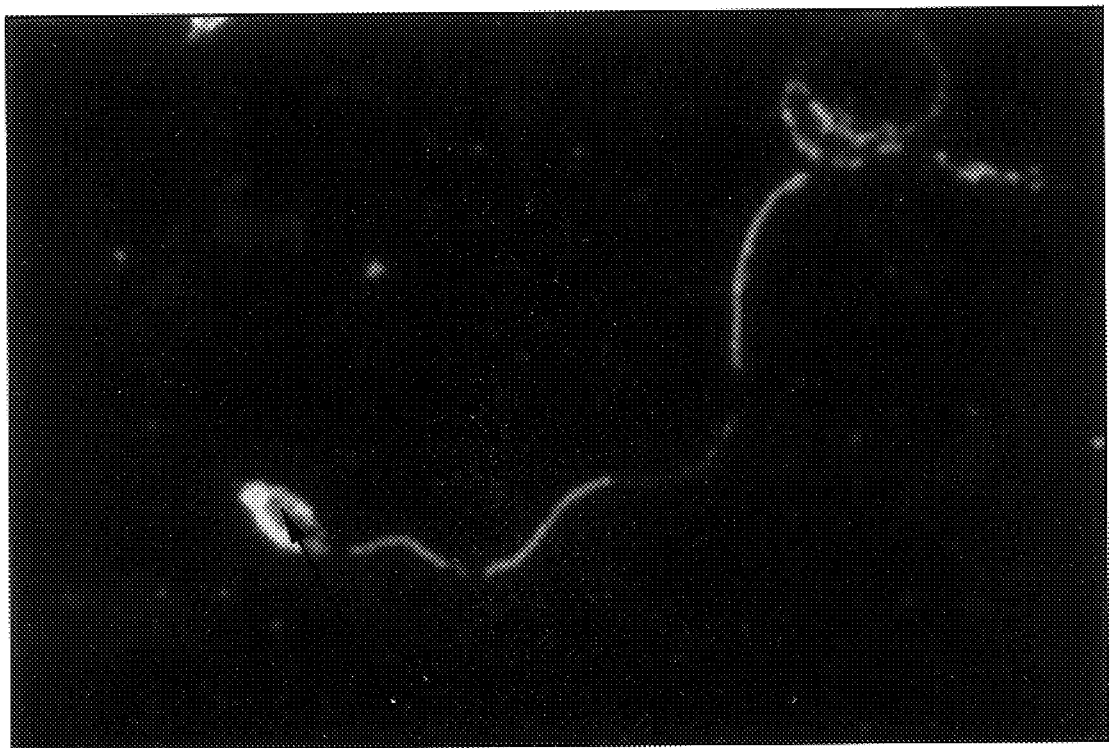
FIGS. 3A & 3B is the MAb 7B3 indirect immunofluorescence detection of GP900 present on the surface FIG. 3A and shed FIG. 3B from the surface of a motile sporozoite.
Figure 3B:
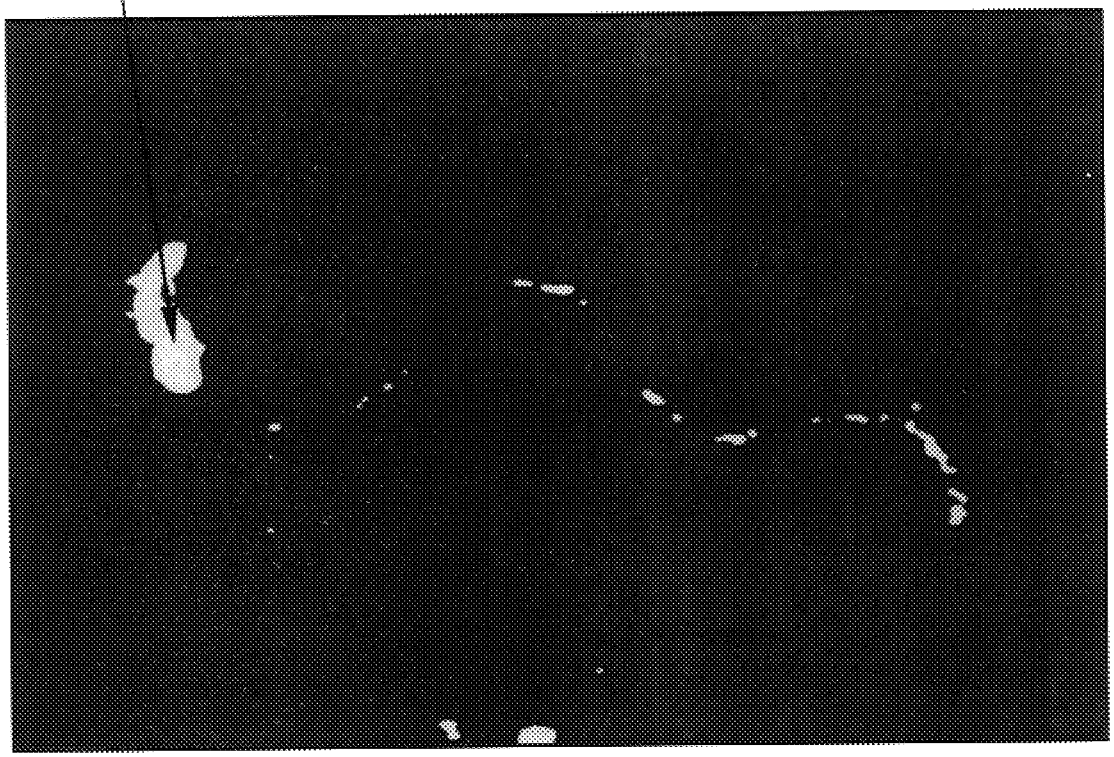

FIG. 3 shows the indirect immunofluorescence detection of GP900 with MAb 7B3 after fixation of the sporozoites with formaldehyde. MAb 7B3 was used because it was previously shown to detect only GP900 on immunoblots of Cryptosporidium sporozoite proteins. FIG. 3A shows that GP900 is present around the living sporozoite and is shed (FIG. 3B) from the posterior aspect of living sporozoites as the sporozoites glide.

In order to show that GP900 is a glycoprotein, N-linked carbohydrate was enzymatically removed from *Cryptosporidium parvum* oocyst/sporozoite proteins and the remaining protein was as separated by SDS-PAGE and detected with MAb 10C6 by an immunoblot. Results are seen in FIG. 4.

Figure 4:
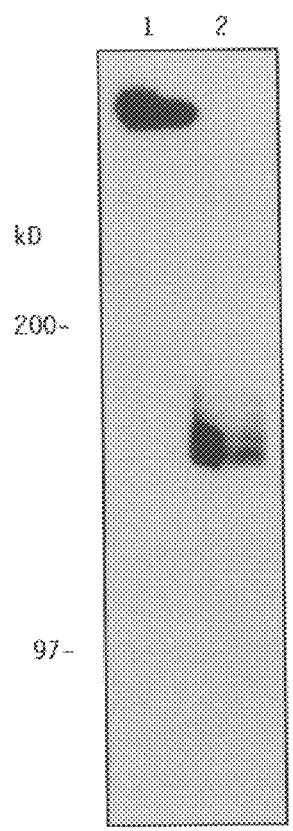
FIG. 4 is the immunoblot of *Cryptosporidium parvum* N-deglycosylated sporozoite/oocyst proteins using monoclonal antibodies to GP900.

FIG. 4 indicates that deglycosylation removes reactivity with MAb 10C6 (1), a GP900 reactive MAb, and generates new reactivities (2) which exhibit a ladder-like pattern between markers having apparent molecular weight 97 and 200. The estimated Mr of those molecular species in this figure are 150,000–180,000. This data is consistent with the removal of N-linked carbohydrate moieties from the GP900 protein backbone and with the appearance of the protein backbone alone or with incomplete removal of all N-linked carbohydrates or O-linked sugars. It is also consistent with potential size polymorphism in the GP900 core protein or combination of these events. From this data the protein core of GP900 would be predicted to have a Mr of 150,000–180,000.

An anti-GP900 polyclonal antibody, affinity purified from oocyst/sporozoite antibodies on the protein expressed by a λgt11 clone S34 using S34 recombinant eluted antibody (S34 REA), also detected a Mr greater than 900,000 protein in intact sporozoites and a ladder of proteins with the smallest at about Mr 150,000 after N-deglycosylation. Cross immunoprecipitation experiments showed that these three reagents, S34 REA, and anti-GP900 polyclonal and monoclonal MAb 10C6 antibodies, detected the Mr >900,000 protein indicating that the S34 clone encodes a portion of the core protein which when glycosylated corresponds to the GP900 protein.

In order to determine the subcellular localization of GP900, anti-GP900 mouse ascites were assayed on LR White Electronmicrograph sections of ileum from experimentally infected rats that contained all developmental stages of the parasite. Results are seen in FIG. 5.

Figure 5:
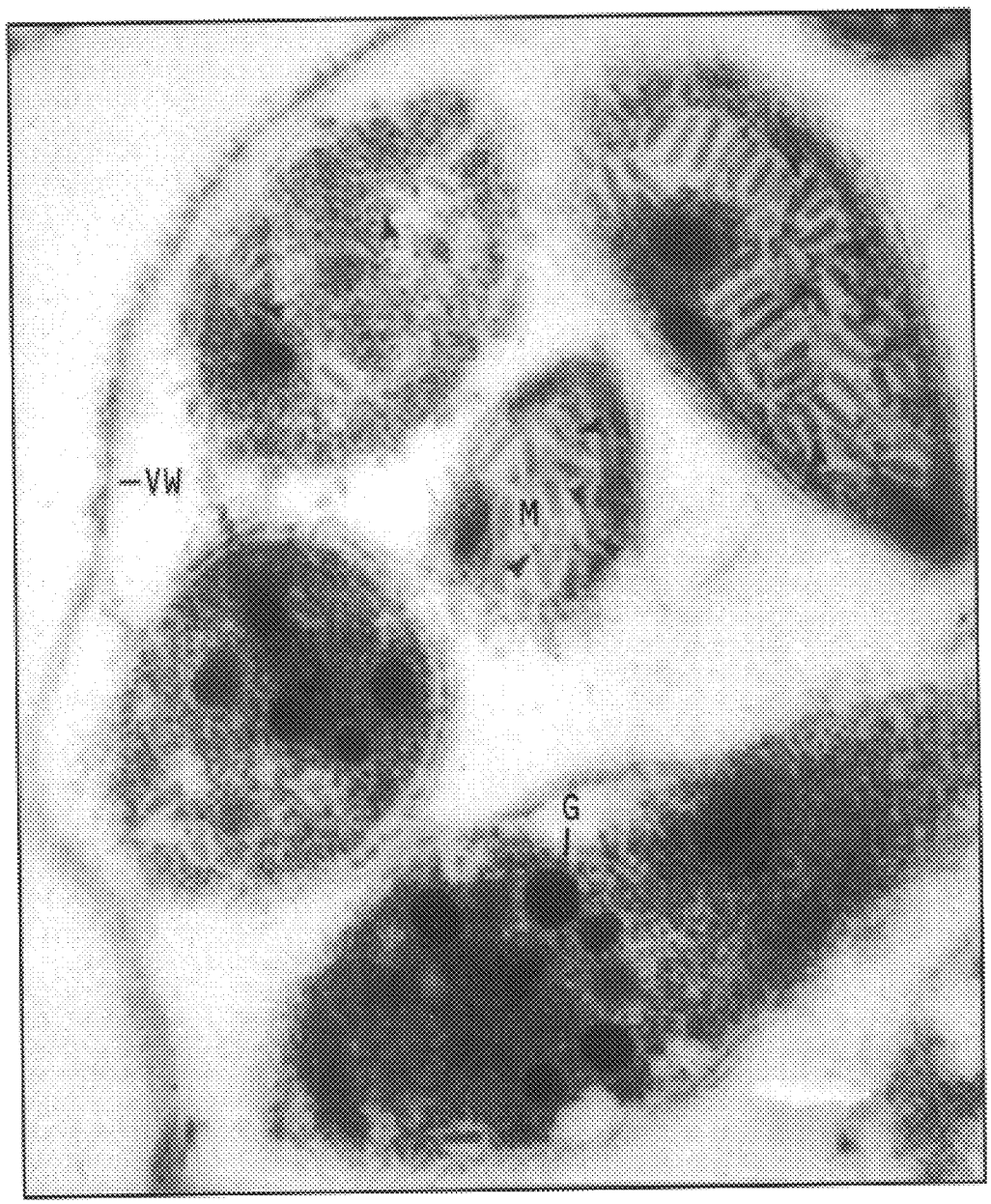
FIG. 5 depicts the electronmicrographic localization of GP900.

In FIG. 5, the micronemes of merozoites (within a developing schizont) appear as stacked plate-like radiolucent structures in which the gold particles of the second antibody, used to localize GP900 polyclonal antibodies, are concentrated. GP 900 was also seen in sporozoites within oocysts (data not shown). The rhoptries and dense granules were not labeled. No surface labeling of sporozoites and merozoites was observed. No gold particles were detected in the parasitophorous vacuole or over the vacuolar wall. No antigen could be detected in host-cell cytoplasm.

B. GP900 Gene Cloning/Sequencing and Genomic Southern Analysis

The GP900 gene of *Cryptosporidium parvum* was isolated from a naturally infected neonatal calf (NINC) isolate. DNA from calves was used to prepare a λgt11 expression library containing clones with an open reading frame for GP900 which is 5164 bp. The sequence of this open reading frame was determined in the following way.

Clone S34 was previously determined to encode a portion of a much larger protein, GP900, using S34 REA. A second GP900 clone, Ag4, reacted with polyclonal anti-GP900 and a MAb to GP900 but the Ag4 and S34 insert DNAs did not cross-hybridize with one another. Upon sequencing, the clones were found to contain distinctly different sequences with no overlap. The inserts were used to double screen the λ genomic library to determine if a clone encoding both could be identified indicating that Ag4 and S34 were collinear portions of the same gene. Clone DB8, which hybridized to both S34 and Ag4, contained a single open reading frame containing both the S34 and the Ag4 sequences. PCR amplification products generated from the 5' and 3' terminal sequences of DB8 were used to identify clones, 95-18 and 93-14, respectively. When added to the DB8 sequence, the sequence generated from these clones comprised the open reading frame which is still open at the 5' end and 3' flanking noncoding region.

Genomic Southern analysis was undertaken to determine if GP900 was encoded by a single gene and if so whether this gene was polymorphic in the three isolates for which the locus was available, namely the NINC isolate and the Iowa and AUCP-1 isolates. DB8 DNA from NINC isolate was used as a probe. The sequence of DB8 contains no EcoRI, Bgl II or Hind III sites but contains many (10) Hind I sites. The larger restriction fragment has a size of 1146 bp and include parts of domains 1 and 2. The short restriction fragment is 741 bp and covers half of domain 3 and all of domain 4. Results are seen in FIG. 6.

Figure 6:
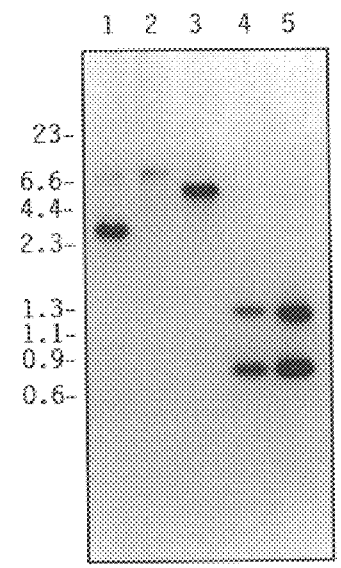
FIG. 6 is the genomic Southern analysis of the GP900 gene fragment.

FIG. 6 is a genomic Southern analysis of the GP900 gene locus. The Southern blot was hybridized with the pDB8 insert. Lanes 1–4 shows the Iowa isolate DNA. Lane 5 shows the AUCP-1 isolate DNA. Lane 1 shows EcoR I digestion. Lane 2 shows Bgl II digestion. Lane 3 shows Hind III digestion. Lanes 4 and 5 show Hind I digestion. No difference in restriction pattern was seen between the Iowa and AUCP-1 isolates in the Hind I digestion lanes.

FIG. 6 shows that the DB8 probe of the NINC Cryptosporidium isolate hybridizes to a single DNA fragment in EcoRI, Bgl II and Hind III digests of the Iowa strand, indicating that GP900 is encoded by a single prominent gene. In lanes 4 and 5 the probe hybridizes to two fragments in the Iowa and AUCP-1 isolate DNA, which are of approximately the same size as the two largest fragments encompassing the two polythreonine regions of the DB8 probe. These data indicate that gross GP900 gene rearrangements have not occurred in the three different isolates studied. This observation is further confirmed by the fact that both the Iowa and AUCP isolates produce a large 900 kDa protein which reacts with the polyclonal antibodies to GP900 initially prepared against the AUCP-1 isolate.

C. Structure of the GP900 Gene and its Encoded Protein

Sequences identified as SEQ ID NO: 1 and 2 are nucleotide sequences of the GP900 gene fragment. The sequence identified as SEQ ID NO: 5 is the corresponding protein.

The GP900 open reading frame encodes two mucin-like polythreonine domains.

Domains 1 and 3 of the protein are cysteine rich domains whereas domains 2 and 4 are mucin-like domains containing large numbers of threonines.

Domain 1 contains 5 cysteine residues. Domain 3 has 6 cysteines. Neither domain is highly homologous to any known sequence in GenBank or Swiss Protein Bank.

Domain 2 is composed of 94% threonine residues including an unusual stretch of 112 uninterrupted threonines. Domain 4 is composed of 56% threonine residues. Both domains also contain repeats of the sequence lysine-lysine-proline or lysine-proline. When the deduced protein sequence was analyzed by searches of the GenBank and Swiss Protein Bank, the greatest similarities were found between the threonine-rich regions of GP900 and other glycoproteins with either proven or putative O-linked glycosylation.

GP900 is both N- and O-glycosylated. GP900 has been shown to be susceptible to treatment with N-glycosidase F (N-glycanase) which cleaves high mannose and complex structures (FIG. 4).

The presence of abundant cysteines on a surface protein of Cryptosporidium which is functionally homologous to the circumsporozoite protein of malaria strongly suggests that these cysteines participate in binding phenomena and may comprise new binding motifs. Numerous apicomplexan parasite proteins, such as plasmodium, CSP, Duffy binding protein, EBA and PFEMPI have binding domains which contain cysteine rich regions. N or O linked carbohydrate moieties may also participate in binding to adjacent cells.

D. Production of GP900 Recombinant Proteins

In order to prepare reagents for specific portions of GP900 to assay their effects on sporozoite adhesion, invasion and intracellular development in vitro and infection in vivo, polyclonal antibodies were made to purified wild type β-galactosidase, Ag4-β-galactosidase and S34-β-galactosidase fusion proteins according to Example 6.

In order to further define these antibodies by removing the reactivity to β-galactosidase and to concentrate them, affinity purified antibodies to the Ag4 and S34 portions of their fusion proteins were prepared according to Example 6. These various antibody preparations were used to probe an immunoblot of proteins from *Cryptosporidium parvum* oocysts/sporozoites. Results are shown in FIG. 7.

Figure 7:
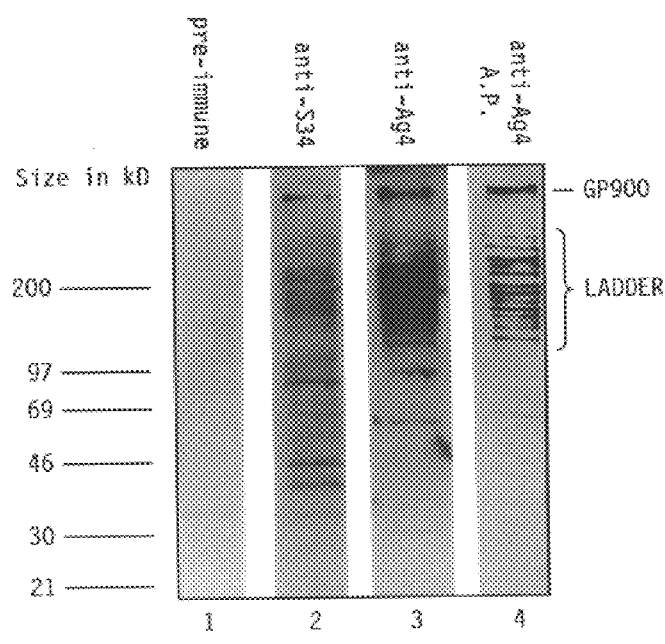
FIG. 7 shows an immunoblot using antibodies to recombinant GP900 proteins.

FIG. 7 is an immunoblot of proteins obtained from *Cryptosporidium parvum* oocysts or sporozoites. Marker size in kDa is indicated. Lane 1 is the S34 antigen probed with pre-immune rabbit serum. Lanes 2–4 are the serum of rabbit immunized with S34 antigen. Lane 2 is probed with anti-S34 antibody. Lane 3 is probed with the polyclonal anti-Ag4 antibody. Lane 4 is probed with the anti-Ag4 affinity purified (A.P.) polyclonal antibody.

FIG. 7, lane 11 shows that the pre-immune serum from the rabbit which received the S34 antigen is mildly reactive to two proteins of *Cryptosporidium parvum*. After immunization with the S34 antigen (lanes 2–4), the antisera react with a whole variety of proteins including GP900, a ladder of proteins ranging in size from 150 to 250 kDa, and several different proteins of lower molecular weight. Since the S34 sequence carries the poly-threonine repeats, it would seem that the antibody which recognizes these repeats will also recognize other proteins with this repeated motif and that the multiple bands represent such cross reactions. However, the results point toward another interpretation. The polyclonal antibody directed against Ag4, which does not carry poly-threonine repeats, and the affinity purified Ag4 antibody, recognize GP900 as well as the ladder of proteins between 150–250 kDa, suggesting that the ladder protein represents the core protein of GP900, not cross-reacting proteins.

E. In Vitro and In Vivo Assessment of Activity of Anti-GP900 and Anti-Recombinant GP900 Antibodies In order to determine whether native or recombinantly produced antibodies in fact inhibit Cryptosporidium infection and would, therefore, be viable reagents for provoking active or providing passive immunity, or be useful for therapeutic purposes, in vitro and in vivo assessments of the effect of native or recombinant antibodies raised against GP900 antigen were investigated.

Antibody mediated inhibition of invasion and intracellular development was studied in Madin Darby Canine Kidney (MDCK) cells.

For these studies, MDCK cell monolayers were infected with *Cryptosporidium parvum* oocysts of the Iowa isolate in the presence of control reagents or immune sera, and colostrum was directed against a series of *Cryptosporidium parvum* oocyst antigens. Antisera and HBC Ig/sham HBC Ig were diluted 1:40 in cell culture media, such as RPMI, except for affinity purified anti-Ag4 which was diluted 1:16. Affinity-purified anti-Ag4 was assayed at a final protein concentration of 75 $\mu$g/ml by the Bradford technique. The protein concentration of HBC Ig 40529 at a 1:40 dilution was 800 $\mu$g/ml. Results are shown on FIG. 8.

Figure 8:
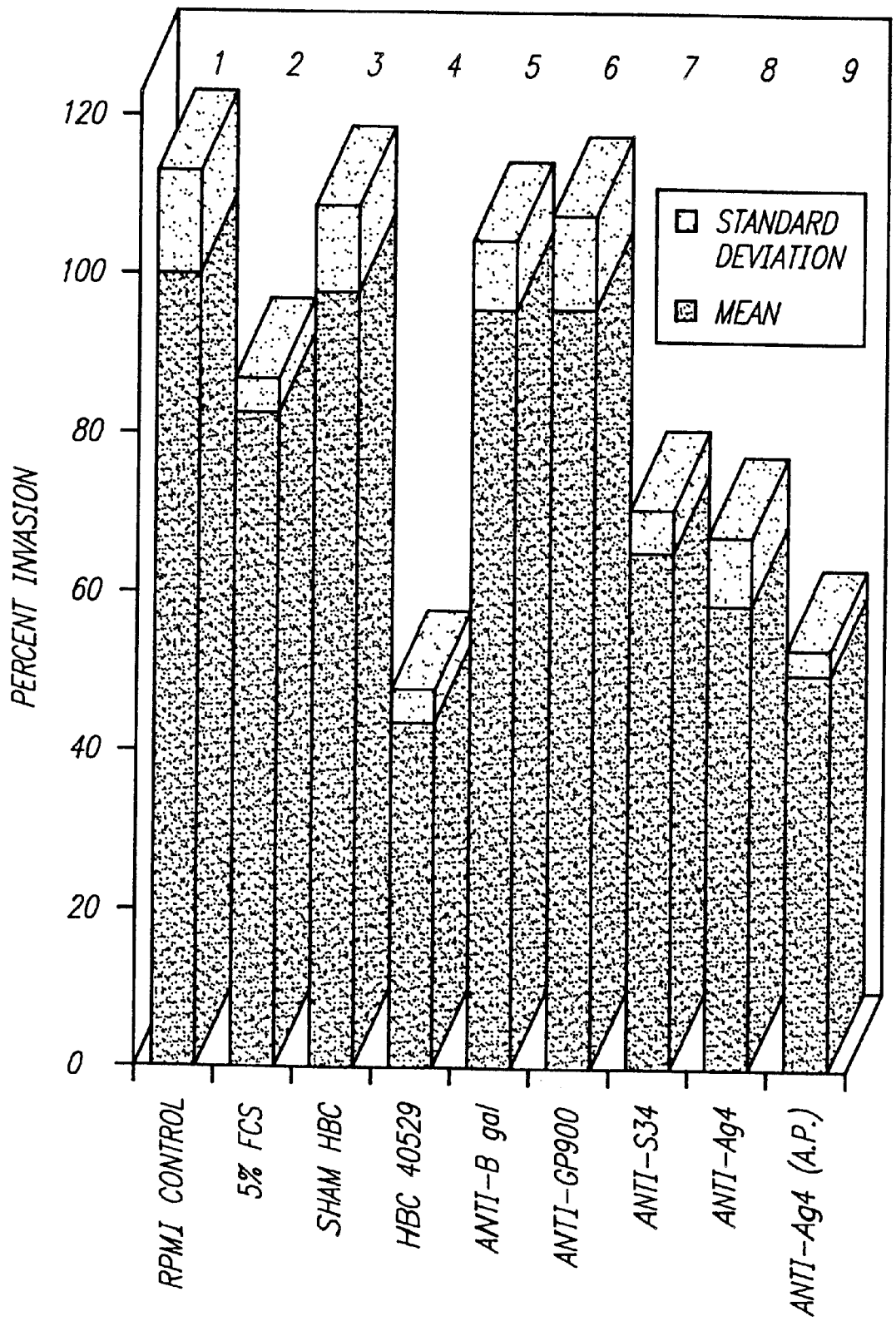
FIG. 8 is a graphical illustration of the inhibition of invasion and intracellular development of MDCK cells in vitro by antibodies to GP900 recombinant proteins.

FIG. 8 is a graph showing *Cryptosporidium parvum* invasion into MDCK cells which were not treated (RPMI control=Bar 1) or were treated with fetal calf serum (bar 2), with sham HBC serum (bar 3), with HBC Ig 40529 serum (bar 4), with anti-$\beta$-galactosidase serum (bar 5), with anti-GP900 serum (bar 6), with anti-S34 serum (bar 7), with anti-Ag4 serum (bar 8) or with anti-Ag4 affinity purified serum (bar 9). Responses are expressed in percent of invasion.

As seen in FIG. 8, inhibition of parasite invasion/intracellular development was observed with antisera raised against protein epitopes of Ag4 (8) and S34 (7) expressed as e-galactosidase fusion proteins. The antibody raised against wild type $\beta$-galactosidase (4) did not confer protection. Negative experimental controls for the inhibition assay included RPMI containing no additives (1), RPMI containing 5% fetal calf serum (2), or sham hyperimmune bovine colostrum (SHAM-HBC) (3), collected from cows immunized with herd vaccines but not with Cryptosporidium. Recombinant S-34-glutathione-s-transferase fusion protein (S34-GST) at 100 nM and 1 $\mu$M preincubated with 1:40 anti-S34-galactosidase (bar 4 shows 1 $\mu$M) abolished the inhibitory activity of the antibody verifying that the specificity of the inhibition is conferred by the S34 protein sequence and the antibody to it.

FIG. 8 clearly shows that the absence of antibodies in controls or the presence of sham HBC anti-$\beta$-galactosidases and anti-GP900 antibodies did not provide protection against Cryptosporidium infectivity, invasion or adhesion. On the other hand, antibodies raised against S34 (bar 7) and against Ag4 (bar 8 and bar 9), whether affinity purified (bar 9) or not (bar 8), provided good protection against Cryptosporidium infection. Affinity purified polyclonal antibody (bar 9) was the most active in this system and almost equal in activity to HBC immunoglobulin.

In order to determine whether the inhibitory response depends on the dose of the antibody, dose response curve of the affinity purified S34 antibodies at concentrations of 10 (bar 5), 50 (bar 6), 100 (bar 7) and 500 (bar 8) $\mu$g/ml, was determined and compared to controls represented by untreated oocysts (bar 1), S34-$\beta$-galactosidase antibodies (bar 2), HBC Ig (bar 3) and anti-oocyst antibodies (bar 4). Response is expressed in parasite-to-host nuclei ratio. Results are seen in FIG. 9.

Figure 9:
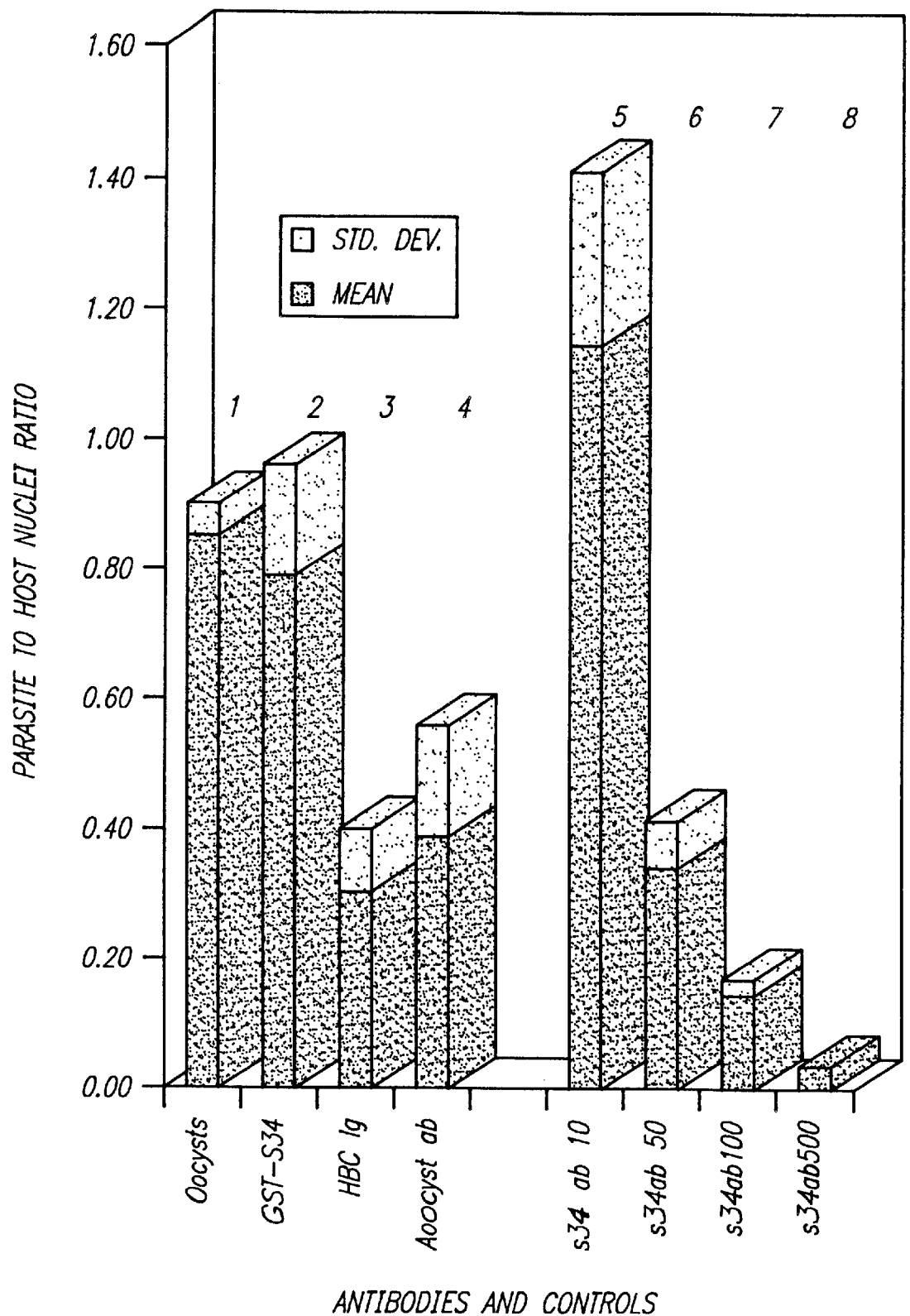
FIG. 9 is a graphical illustration of the dose-dependent inhibition of sporozoites invasion/intracellular development in MDCK cells in vitro by affinity purified anti-S34 antibody.

As seen in FIG. 9, 50 $\mu$g/ml of anti-S34 antibody provided more than 50% protection while 100 $\mu$g/ml and 500 $\mu$g/ml provided excellent to almost complete protection against invasion and intracellular development of Cryptosporidium sporozoites. These results further demonstrate the specific nature of the antibody/antigen reaction.

In order to determine whether the native or recombinant antibodies raised against Cryptosporidium antigen GP900 or a fraction thereof are able to inhibit Cryptosporidium infection in vivo, the anti-S34-$\beta$-galactosidase and anti-S19-$\beta$-galactosidase antibodies were tested in a neonatal mice model. Results are seen in FIG. 10.

Figure 10:
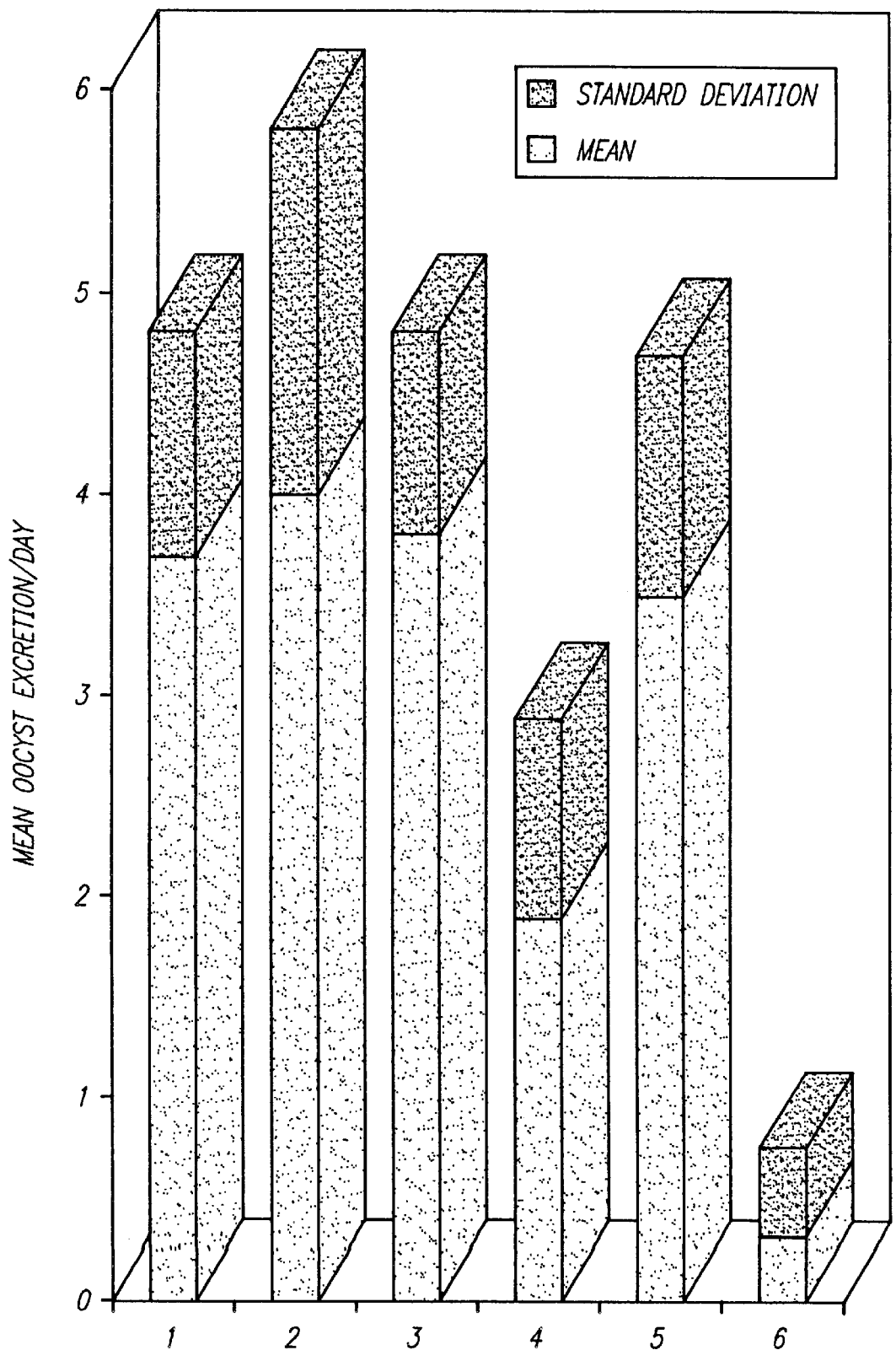
FIG. 10 is a graphical illustration of the inhibition of parasite burden in vivo in neonatal mice challenged with Cryptosporidium and treated with oral anti-recombinant GP900 antibodies.

FIG. 10 shows the in vivo effect of antibodies to GP900 recombinants on shedding of oocysts by neonatal mice infected with Cryptosporidium.

FIG. 10 is a graph representing the amount of excretion of Cryptosporidium oocysts per day in mice treated with phosphate buffered saline (bar 1); anti-$\beta$-galactosidase (bar 2); anti-Ag4-$\beta$-galactosidase (bar 3); anti-S34-$\beta$-galactosidase (bar 4); 1:5 HBC Ig 40529 (bar 5); and paromomycin (bar 6). As seen in FIG. 10, anti-S34 (bar 4) reduced the oocysts shed by about 500 relative to control PBS (bar 1) and anti-$\beta$-galactosidase antibody (bar 2). Although crude antisera was used, antibody to S34 -galactosidase inhibited shedding by about 50% relative to control treated with PBS and anti-$\beta$-galactosidase antibody. The inhibition was superior to the inhibition conferred by a 1:5 dilution of HBC Ig 40529 (bar 5), the positive control antibody which had previously been shown to prevent cryptosporidial disease in calves challenged with Cryptosporidium (*Infect. Immun.*, 61:4079–4084 (1993)).

From the results obtained in these experiments, it is clear that clone S34 encodes a Cryptosporidium antigen and that the antibodies specifically raised against this antigen are able to inhibit the Cryptosporidium infection in vivo.

In order to determine whether GP 900, like the circumsporozoite protein of malaria, is an adhesion glycoprotein mediating the attachment of the sporozoite to a cell of GI origin, a paraformaldehyde fixed CaCO-2 cell adhesion assay was used to assess antibodies to β-galactosidase, Ag4-β-galactosidase and S34-β-galactosidase, as described in Example 13. In this assay, the same magnitude of inhibition of adhesion of Cryptosporidium sporozoites to CaCO-2 cells (mean O.D. 50% of control in ELISA) with a 1:50 dilution of anti S34-β-galactosidase was conferred as was observed in the in vitro invasion and intracellular development assay in living MDCK cells by a 1:40 dilution of the same antibody as seen in FIG. 8.

In addition, these results were comparable to those seen when a 1:100 dilution of anti-Cryptosporidium murine ascites (48% inhibition) a polyclonal rabbit anti-Cryptosporidium antiserum (inhibition 51%) were previously assayed in this system (data not shown). Similarly to the in vivo model, in this in vitro model, the anti-Ag4-β-galactosidase also did not inhibit invasion and infection development. However, anti-S34 inhibited invasion/intracellular development in living MDCK cells in vitro, adhesion in killed CaCO-2 cells in vitro and infection in vivo in mice. These results support the premise that a biological function is inhibited by anti-S34 antibodies in the in vitro and in vivo systems and that that function is adhesion. Additionally, these results show that antibodies to recombinant GP900 correlate significantly with the inhibitory activity of HBC Ig 40529 and anti-Cryptosporidium antibodies from mouse and rabbit sources.

The antigen has been deduced to have an amino acid sequence depicted by SEQ ID NO: 5 and was encoded by genomic DNA sequences depicted by SEQ ID NO: 1. Antibodies against the recombinant S34 protein are able to significantly inhibit Cryptosporidium infection in vitro and in vivo.

Consequently, the results described above indicate the usefullness of the anti-S34 antibody for both anti-Cryptosporidium prophylaxis and therapy of a human or animal host.

2. P68 Protein, Recombinant Protein and DNA/RNA
A. Identification of the Cryptosporidium Antigen designated P68

A Cryptosporidium antigen designated P68 is an apical protein of sporozoites and merozoites. The protein has a size of between about 50–100 kDa. The P68 protein consists of 503 amino acids and its amino acid sequence is depicted as SEQ ID NO: 6. The P68 protein is derived from the gene S19. The DNA sequences encoding the P68 protein are depicted as SEQ ID NO: 3 and 4.

B. Cloning/Sequencing and Genomic Southern Analysis of the Gene for P68

The purification and initial characterization of the S19 clone and the description of the restriction fragment genomic expression library from which it was isolated have been described in (*Infect. Immun.*, 60:5132–5138 (1992)). A recombinant eluted antibody from the clone identified a dominant 68 kDa protein on Western blot (FIG. 11) of oocyst sporozoite proteins and was localized to the anterior end of the sporozoite by indirect fluorescent antibody analysis.

Figure 11:
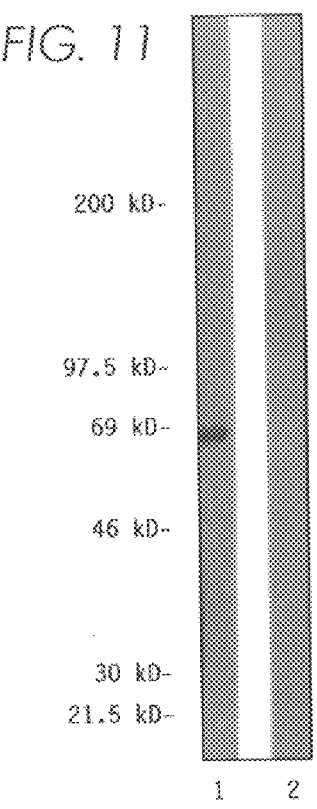
FIG. 11 is an immunoblot of *Cryptosporidium parvum* oocyst/sporozoite proteins using polyclonal antibodies to P68.

FIG. 11 is an immunoblot of AUCP isolate oocyst/sporozoite proteins. Lane 1 was detected with polyclonal anti-sporozoite/oocyst antibodies which had been affinity purified on the S19 fusion protein (S19-REA). As seen in FIG. 11, an immunoblot with the antibody identified the protein of Mr less than 69 kDa marker, known as 68 kDa protein. Lane 2 is REA prepared on wild type β-galactosidase as a negative control.

The S19 insert was subcloned into Bluescript and sequenced as described in Example 17. The insert was used as a molecular probe to identify λgt11 expression library clones which extended 5' and 3' from S19. A 2380 bp locus was defined. The defined portion of the locus has 1509 bp of open reading frame which remains open at the 5' end.

C. Structure of the Gene and its Encoded Protein

The sequences of the P68 gene fragment are shown in SEQ ID NOs: 2 and 3. The sequence of the corresponding protein is given in SEQ ID NO: 6.

D. Production of P68 Recombinant Proteins

Using essentially the same methods as described for GP900 and for clones S34 and Ag4, S19 was subcloned into the pGEX expression vector to yield the expression clone GST-S19, a recombinant protein fused to glutathione S transferase. Antibodies were raised to GST-S19 in two rabbits and to the native GST, according to methods described in Examples 4 and 5.

E. In Vitro and In Vivo Assessment of Activity of Anti-P68 Antibody

Antibodies were assayed in vitro and in vivo for inhibition of invasion and inhibition of infection, respectively, as described in Examples 11 and 14. Results are seen in FIGS. 12 and 13.

Figure 12:
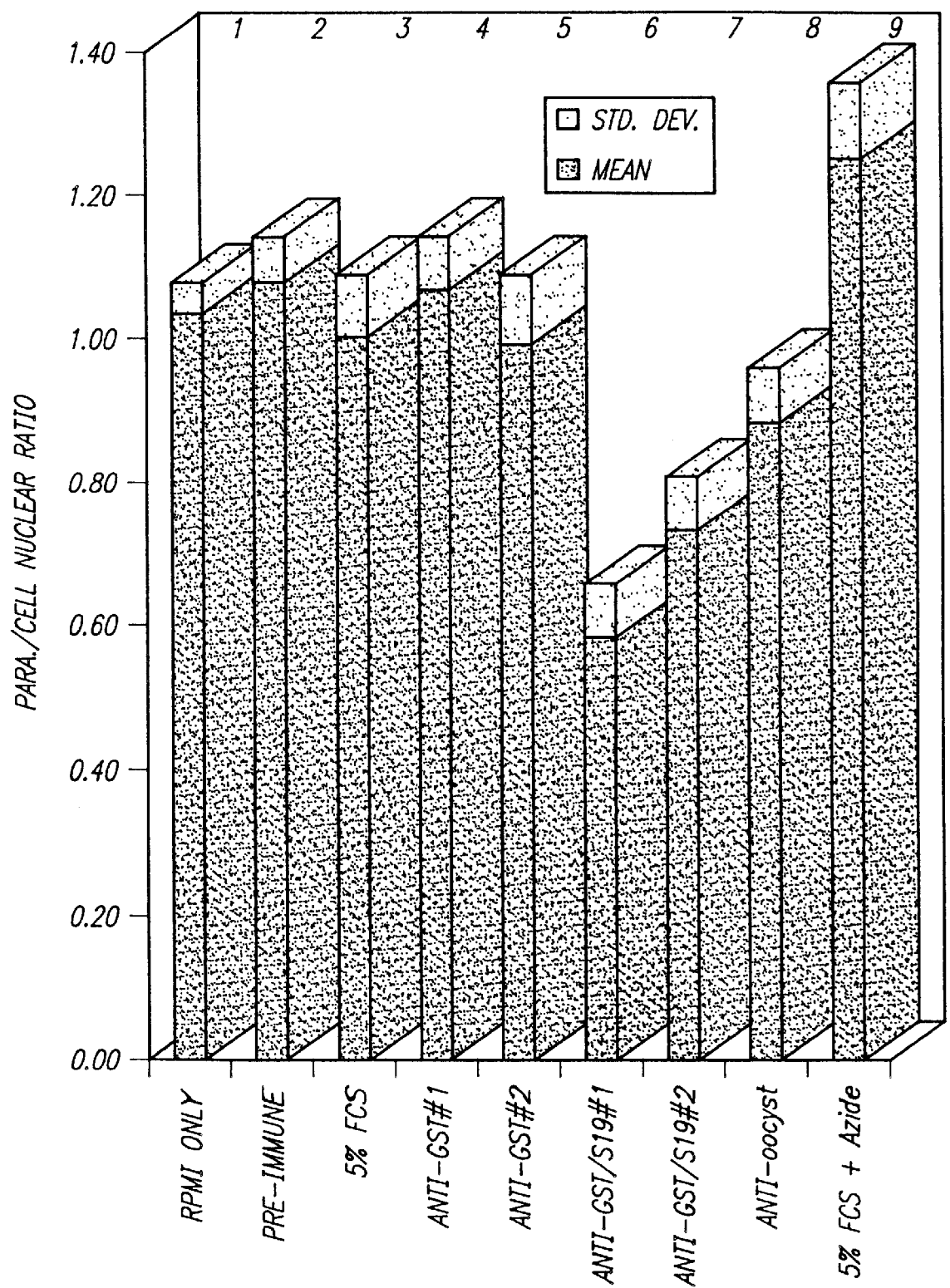
FIG. 12 is a graphical illustration of the inhibition of invasion and intracellular development of MDCK cells in vitro by antibodies to P68 recombinant protein.

The graph seen in FIG. 12 shows inhibition of invasion and intracellular development by antibodies to P68 expressed as parasites/MDCK cell nuclear ratio. All antibodies were at a dilution of 1:40 except FCS.

As seen in FIG. 12, controls such as RPMI medium (bar 1), preimmune serum (bar 2), 5% FCS (bar 3), and anti-GST fusion protein (bar 4) and (bar 5) antibodies raised against native GST were not effective in inhibiting Cryptosporidium infection. The two anti-GST/S19 (bar 6) and (bar 7) antibodies raised against a recombinant fusion protein of S19-glutathione-s-transferase clone inhibited the Cryptosporidium invasion by 46% and 33% relative to control. Both were more inhibitory than an anti-oocyst/sporozoite (bar 8) antibody made in rabbits. The anti-GST antibodies, preimmune antibodies and 5% fetal calf serum (FCS), did not inhibit invasion and intracellular development.

Figure 13:
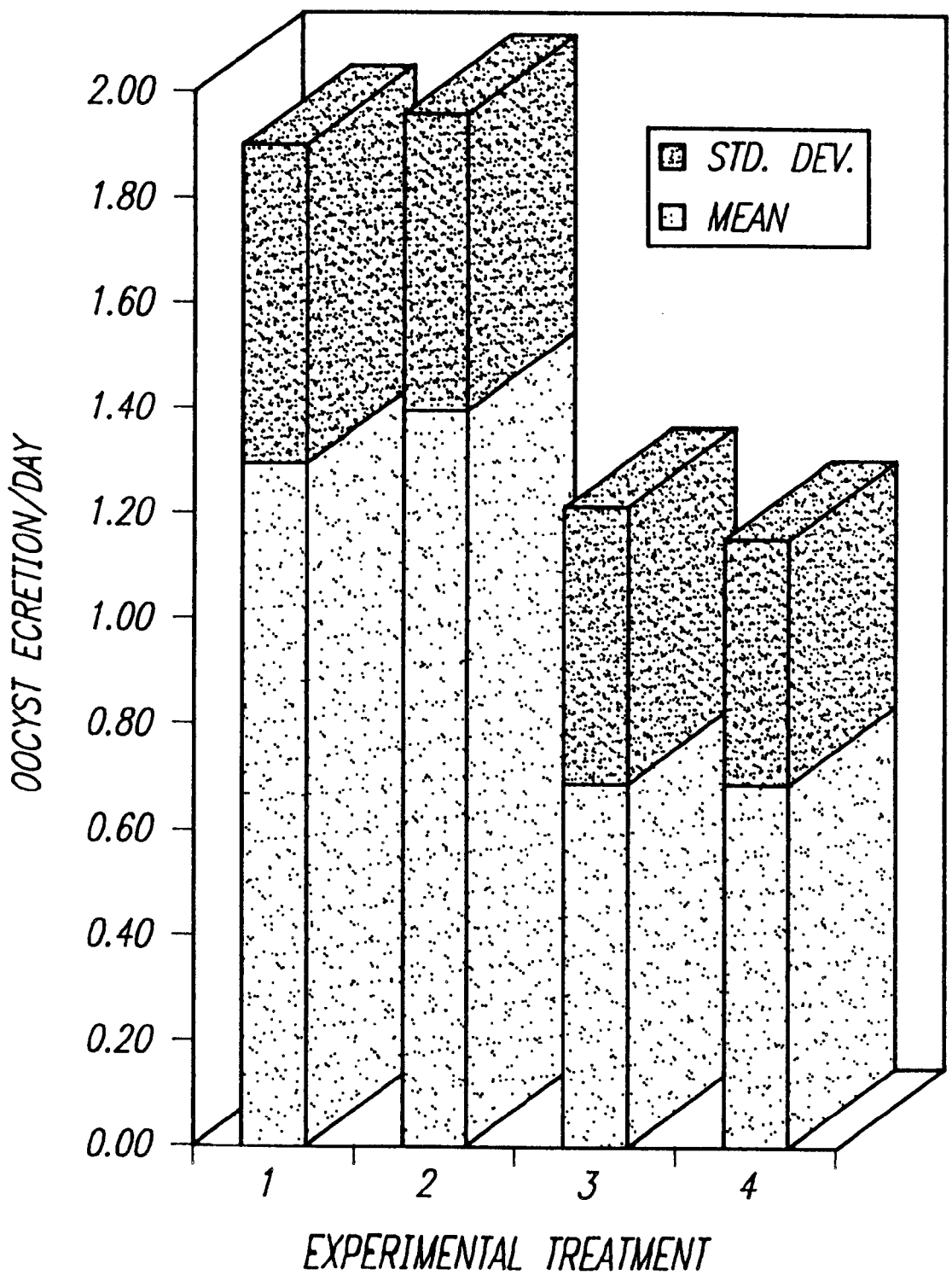
FIG. 13 is a graphical illustration of the inhibition of parasite burden in vivo in neonatal mice challenged with Cryptosporidium and treated with oral anti-recombinant P68 antibodies.

FIG. 13 is a graph showing the effect of anti-S19 antibody on oocyst excretion in vivo in a CD neonatal mouse model as described in Example 14. FIG. 13 shows that antibodies to S19-GST raised in two rabbits (bar 3) and (bar 4) significantly decreased oocyst excretion as compared to animals treated with anti-GST antibody (bar 2) or without treatment (bar 1).

II. Mucosal and Systemic Lymphoproliferative Responses

In order to evaluate the immune response to Cryptosporidium infection in HIV infected or in healthy individuals, mucosal and systemic lymphoproliferative responses were studied using recombinant GP900 stimulation of mucosal lymphocytes in the gastrointestinal mucosa of a rhesus macaque infected with SIV and Cryptosporidium which did not have the clinical disease. This model was established to determine what type of mucosal responses are correlated with resistance to the clinical disease.

The exact experimental conditions are described in Example 15. Briefly, a rhesus macaque mucosal immunity model was developed to evaluate the immune response to Cryptosporidium in normal and in HIV infected individuals. A mucosal lymphocyte proliferation experiment, results of which are shown and described in Tables 1 and 2, monitored $^3$H uptake of cultured lymphocytes harvested at necropsy from the duodenum/jejunum, ileum, and colon of a clinically well, (no weight loss, no diarrhea) SIV-infected macaque, experimentally Cryptosporidium infected rhesus with a low CD4 count of 250/mm$^3$. The animal intermittently excreted oocysts. The experiment was designed to look at T cell stimulation and used concanavalin A (con A) as a T cell mitogen control, but did not include a B cell mitogen control.

TABLE 1

PROLIFERATION OF GASTROINTESTINAL MNCs BY SPECIFIC ANTIGEN

| A. Cell Origin | Unstimulated (mean cpm) | US standard deviation | Con A (mean cpm) | Con A standard deviation | S.I. |
|---|---|---|---|---|---|
| Duo/Jej IEL | 743 | 293 | 2602 | 130 | *3.52 |
| Duo/Jej LPL | 640 | 30.7 | 151 | 31 | 0.23 |
| Ileum IEL | 834 | 32.8 | 4021 | 544 | *4.8 |
| Ileum LPL | 633 | 102 | 175 | 45 | 0.27 |
| Colon IEL | 1170 | 457 | 2355 | 39.5 | *2.0 |
| Colon LPL | 556 | 26 | 272 | 14.8 | 0.48 |
| Spleen | 8726 | 204 | 143,588 | 1810 | *16.4 |

| B. Cell Origin | Unstimulated (mean cpm) | US standard deviation | Spz Ag (mean cpm) | Spz Ag standard deviation | S.I. |
|---|---|---|---|---|---|
| Duo/Jej IEL | 333 | 55 | 296 | 75 | 0.88 |
| Duo/Jej LPL | 644 | 40 | 304 | 103 | 0.47 |
| Ileum IEL | 500 | 144 | 388 | 96 | 0.77 |
| Ileum LPL | 627 | 130 | 286 | 50 | 0.45 |
| Colon IEL | 285 | 9.5 | 300 | 1.1 | 1.05 |
| Colon LPL | 891 | 62.5 | 521 | 62 | 0.58 |

| C. Cell Origin | Unstimulated (mean cpm) | US standard deviation | S34 (mean cpm) | S34 standard deviation | S.I. |
|---|---|---|---|---|---|
| Duo/Jej IEL | 333 | 55 | 185 | 49 | 0.55 |
| Duo/Jej LPL | 644 | 40 | 1902 | 574 | *2.95 |
| Ileum IEL | 500 | 144 | 201 | 49 | 0.4 |
| Ileum LPL | 627 | 130 | 4357 | 403 | *6.9 |
| Colon IEL | 285 | 9.5 | 497 | 121 | 1.7 |
| Colon LPL | 891 | 62.5 | 14720 | 3003 | *16.5 |

| D. Cells Origin | Unstimulated (mean cpm) | US standard deviation | S19 (mean cpm) | S19 standard deviation | S.I.S. |
|---|---|---|---|---|---|
| Duo/Jej IEL | 333 | 55 | 500 | 22.8 | 1.5 |
| Duo/Jej LPL | 644 | 40 | 537 | 79 | 0.83 |
| Ileum IEL | 500 | 144 | 1016 | 134 | *2.03 |
| Ileum LPL | 627 | 130 | 478 | 144 | 0.76 |
| Colon IEL | 285 | 9.5 | 1347 | 394 | *4.72 |
| Colon LPL | 891 | 62.5 | 720 | 126 | 0.8 |

Table 1 shows the incorporation of $^3$H by unstimulated mononuclear cells (MNCs) as mean counts per well and the incorporation in the presence of the T cell mitogen concanavalin A, sporozoite antigen at 10 μg/well, S34-GST antigen at 10 μg/well or S19-GST antigen at 10 μg/well. MNCs were evaluated as a function of site in GI tract that is duodenum/jejunum, ileum or colon, and compartment of mucosa (LPL=lamina propria lymphocytes; IEL= intraepithelial lymphocytes).

S.I. is the stimulation index, expressed as the ratio of the stimulated to unstimulated wells. Values of S.I. greater than 2–3 are considered evidence of significant stimulation.

Results were obtained in quadruplicate with single outlying values discarded.

TABLE 2

SUITABLE PROLIFERATION OF SPLEEN CELLS BY SPECIFIC ANTIGEN

| Antigen | Unstimulated | US standard | Stimulated | S standard | S.I. |
|---|---|---|---|---|---|
| Spz Ag | 1619 | 428 | 2658 | 36 | 1.64 |
| S19 | 1619 | 428 | 3158 | 51 | 1.95 |
| S34 | 1619 | 428 | 1336 | 51 | 0.82 |
| GST | 1619 | 428 | 1700 | 278 | 1.05 |
| Con A | 8726 | 204 | 143,588 | 1810 | *16.4 |

Table 2 reports data for spleen MNCs, representative of the systemic immune system of the same animal. Data found during these experiments shows that although spleen cell (systemic lymphocytes) responded to the T cell mitogen with a significant proliferation, they did not respond to the sporozoite antigen (Spz Ag), S19-GST (S19), S34-GST (S34) or the control peptide GST, indicating that there was no systemic proliferative response in the face of known Cryptosporidium infection without disease.

Mucosal lymphocytes did respond to the recombinant antigens S34 and S19 with significant proliferative responses in a compartment specific manner, (S34 in LPL, S19 in IEL compartments) indicating active mucosal immune responses to these antigens in the face of SIV infection in a clinically healthy animal with intermittent shedding of Cryptosporidium.

Previous studies in rhesus macaques indicated that intraepithelial lymphocytes (IELS) are primarily T cells and lamina propria lymphocytes (LPLs) are predominantly B cells. Evaluation of the FAC cell marker profiles of stimulated cells in each compartment of animals like this is expected to shed light on the type of mucosal immune response which is protective in rhesus macaques. Germane to the current application, the observation that both S19 and S34 stimulated MNCs at concentrations of antigens which did not lead to proliferation in the presence of whole sporozoite antigen indicate that both antigens stimulated the mucosa of this immunocompromised animal and might be viable immunogens for active immunization of immunocompromised animals.

These results suggest that GP900 and P68 epitopes contained in S34 and S19, respectively, stimulate lymphoproliferation of mucosal PMNs.

A second rhesus macaque that was SIV and Cryptosporidium infected remained clinically well but developed diarrhea and was excreting Cryptosporidium as her blood CD4 count fell below 100/mm$^3$. Lymphoproliferative responses to sporozoite antigens, S34-GST, S19-GST, GST and concanavalin A, could not be detected in the blood, spleen, or either compartment of the gastrointestinal mucosa. However, ELISPOT analysis, in which B cells secreting antibodies to specific antigens are detected, showed that some LPLs cells still retained the ability to secrete antibodies to S34-GST and sporozoite antigens assayed at 5× the S34-GST concentration, but not to GST.

This indicates that the proliferative response to S34 and sporozoite antigen was lost at a time when the animal was becoming clinically ill and still had B cells which recognized GP900. These findings suggest that the cytokines necessary for a vigorous B cell response to foreign antigen had been lost.

These results, when taken together with the observations from the first animal, suggest that Cryptosporidium infection may cause chronic diarrhea when the mucosal proliferative response to cryptosporidial antigens ceases, with a fall in production of the antibody in the lamina propria to specific Cryptosporidium antigens to subprotective levels.

III. In vitro Inhibition of *Cryptosporidium parvum* Infection

The in vitro inhibition of the invasion and intracellular development of Cryptosporidium described in Example 11 for GP900 and in Example 18 for P68 protein was shown to occur as a function of anti-Cryptosporidium titer. This was evidenced by its correlation with the corresponding immunoglobulin concentration in protective colostrum (HBC), and by the lack of biological activity of SHAM colostrum (SHAM-HBC). In a supportive experiment described in Example 13, HBC Ig was also shown to significantly inhibit *Cryptosporidium parvum* adhesion in the CaCO-2 cell line, thus providing a potential mechanism for inhibition of invasion and infection.

The in vitro ability of HBC to prevent Cryptosporidium infectivity was shown to be mediated only by specific anti-Cryptosporidium antibodies eluted from Cryptosporidium. Elution from fetal calf serum and SHAM-colostrum did not produce inhibition of the infection.

The studies conducted in support of this invention show that antibodies to specific Cryptosporidium antigens are also responsible for the in vitro effect of the HBC Ig fraction. Additionally, the inhibition in the in vitro assay correlates well with the effect of HBC and HBC Ig in vivo. These results validate the in vitro MDCK cell model as a model for detecting antibodies which were found to be protective in vivo.

Antibodies raised to the fusion proteins of several of the antigens of the invention were found significantly inhibitory in the in vitro MDCK cell model. This finding was then confirmed by similar results obtained with another epithelial cell line, Madin Darby Bovine Kidney (MDBK) cells. These in vitro results indicated that these antibodies by correlation of in vitro results to in vivo systems, would be protective in vivo. This was later confirmed in the in vivo studies.

IV. In vivo Inhibition of *Cryptosporidium parvum* Infection

Studies of the inhibitory effect of the polyclonal antibody of the invention on the *Cryptosporidium parvum* infection in vivo were performed according to the procedure described in Example 17.

HBC 40529 obtained from ImmuCell Corporation (Portland, Me.) was used as a positive control in the animal protection studies described in Example 14 and the HBC Ig of the same lot was also used in the in vitro inhibition studies. Assessment of in vivo efficacy of HBC was performed in newborn, colostrum deprived, Holstein calves challenged with oocysts of *Cryptosporidium parvum*. The efficacy of the immune colostrum preparation for protecting the treated calves from *Cryptosporidium parvum* infection was demonstrated in statistically significant differences between treated and control animals in cumulative fecal scores ($p<0.01$ by one tailed t test) and dehydration scores ($p<0.01$ by one tailed t test) (*Infect. Immun.*, 61:4079–4084 (1993)).

As was originally described in the parent application, Ser. No. 07/891,301, incorporated hereby by reference, no dehydration occurred in the treated group whereas all of the calves in the control group showed some signs of dehydration. The oocyst output was dramatically reduced in the treated group ($<10^3$ oocysts per total fecal output, the limit of detection) when compared to the control group (geometric mean oocyst output=$5.62 \times 10^8$).

These results clearly show that the immune colostrum treatment effectively reduced the initial colonization by *Cryptosporidium parvum* parasites and suppressed the intestinal proliferation of the *Cryptosporidium parvum* parasites which were not initially neutralized.

When similar studies were performed in mice with antibodies to recombinant proteins from the GP900 locus, significant inhibition of infection relative to the positive antibody control (HBC) as well as the negative control was demonstrated with anti-S34, but not with anti-Ag4 or anti-β-galactosidase. Anti-S34 inhibited invasion by 54% percent, whereas the positive control, 1:20 HBC Ig 40529, inhibited by 23% relative to PBS control. This study and the findings confirm that recombinant protein S34 is an effective antigen for the production of passive and active immune products for immunization, prophylaxis and treatment of Cryptosporidium infections.

V. Antibodies and Their Production

Polyclonal or monoclonal antibodies to native or recombinant protein or a glycoprotein of the invention are useful for treatment by providing a protection against Cryptosporidium infections.

Anti- *Cryptosporidium parvum* polyclonal antibodies recognizing the cloned polypeptides are preferred over monoclonal antibodies because they recognize multiple epitopes on the target polypeptide.

According to the method of the current invention, large amounts of recombinant polypeptides are easily produced which enable production of a corresponding large quantity of polyclonal antibodies or of the immunogen for active immunization.

The antibodies to recombinant expressed protein can also be produced according to the invention using the standard method available for production of the antibodies to native protein. Some of these method are described in Examples 2, 4, and 5.

VI. Sequences

Six sequences identified as SEQ ID NO 1–6 are disclosed in this invention. These sequences were prepared according to methods described in Examples 10 and 17.

SEQ ID NO: 1 is a DNA sequence of the open reading frame (ORF) of the antigen designated GP900. The sequence comprises 5164 base pairs.

SEQ ID NO: 2 is a DNA sequence of the ORF of the antigen designated GP900 and its 3' flanking region and comprises 5319 base pairs.

SEQ ID NO: 3 is a DNA sequence of the ORF of the antigen designated P68. The sequence comprises 1509 base pairs.

SEQ ID NO: 4 is a DNA sequence of the ORF denoted P68 and its 3' flanking region and comprises 2380 base pairs.

SEQ ID NO: 5 is an ORF sequence of the protein antigen designated as GP900. The GP900 protein contains 1721 amino acids.

SEQ ID NO:6 is an amino acid sequence of the fragment of protein antigen designated as P68. The P68 protein contains 503 amino acids.

VII. Variants and Mutants

Polymorphism found in GP900 is seen in Table 3.

Table 3 represents variant and mutant sequences of resulting proteins.

As seen in Table 3, domains 2 and 4 of the GP900 DNA contain extensive trinucleotide repeats which are expressed as threonine repeat regions. Similar regions occur and have been characterized in the genes responsible for a number of inheritable genetic diseases of man including fragile X syndrome. Insertions and deletions in these regions which are reflected in the translated protein are known to occur. In addition, decreased amount of protein translation has been shown to occur. These protein abnormalities are thought to be related to impaired function of DNA repair enzymes and polymerases in regions of perfect repeats.

A method producing amplified mutants and variants is described in Example 22. Specific variants and mutants vis-a-vis NINC domain 2 of the SEQ ID NO: 5 are shown in Table 3.

TABLE 3

Conservatively Modified Mutants and Variants of SEQ ID NO: 5

```
SEQ ID 7  Var

TABLE 3-continued

Conservatively Modified Mutants and Variants of SEQ ID NO: 5

V = val
K = lys
M = met

NINC sequence seen in the Table 3, corresponds to amino acids 175–423 of the SEQ ID NO: 5. Mutations and variations of the GP900 protein occur within the NINC domain sequence. Corresponding DNA mutations and variations of the NINC bases domain occur in the DNA sequence nt 524–1270 of the SEQ ID NO: 1 and SEQ ID NO: 2.

VIII. Biologically Derived or Recombinant Anti-Cryptosporidium Vaccines

Vaccine is a biologically derived or recombinantly prepared agent useful for artificially acquired immunization in a host. The current invention describes the production of biologically derived and recombinant vaccines for active immunization of animals and humans against cryptosporidiosis and the preparation of passive immune products for treatment of established infections.

The scope of the invention is, therefore, intended to include biologically derived or recombinantly prepared vaccines based on the antigens of the invention.

A recombinant vaccine is produced by identifying the relevant antigen or antigens of Cryptosporidium, cloning them and expressing them using suitable vectors. This approach yields immunogens which are reproducible in sufficiently large quantities to allow preparation of a vaccine for active immunization. Recombinant vaccines are useful for immunization of the potential Cryptosporidium host, such as for inoculation of cows, to produce the host's own antibodies against a Cryptosporidium infection. Additionally, the recombinant vaccines may be used for production of passive immunotherapeutic agents. For example, when the cow is inoculated with the vaccine, it begins to produce hyperimmune colostrum. Hyperimmune colostrum from these cows is then purified to yield Ig for passive immunotherapy of immunocompromised persons, primarily AIDS patients.

These vaccines are also useful for widespread use in calves to provide primary protection against Cryptosporidium infection. Providing the herd with anti-Cryptosporidium immunity decreases the risk for waterborne outbreaks of cryptosporidiosis in areas where the watershed includes dairy lands. This provides a secondary benefit to humans in those areas. In addition, DNA or RNA may be introduced into a host so that propagation and/or expression of the encoded protein occurs in the host ("a foreign expression system".)

The anti-Cryptosporidium vaccine of the invention contains a Cryptosporidium antigen identified by the invention, modified in such a way that it is incapable of producing the Cryptosporidium symptoms but is capable of eliciting the production of specific protective antibodies against the disease when introduced in the body. A DNA or RNA vaccine for prevention and treatment of infections caused by protozoan Cryptosporidium species (Cryptosporidium) in humans and other mammals was developed by utilizing newly identified and isolated DNA (SEQ ID NOs: 1–4) and amino acid (SEQ ID NOs: 5 and 6) sequences of the Cryptosporidium pathogen designated GP900.

The antigen proteins used for preparation of vaccines correspond to GP900 or to its fragment, or to P68 antigen or its fragment, which are identified by being a target of the polyclonal or monoclonal antibodies of the invention capable of preventing or ameliorating the disease and preventing invasion and/or intracellular development in host cells.

A hybrid vector comprising a DNA segment that encodes the protein antigen able to bind selectively and specifically to anti-Cryptosporidium antibodies operatively coupled to the vector was prepared and expressed. This includes preparation of recombinant vaccines using the viral expression vector outside of the host body and the preparation of DNA vaccines and procaryotic or eukaryotic hosts carrying the hybrid vector which may be introduced into the vertebrate host or a direct introduction of DNA or RNA into host cells generating the host's own expression or translation of DNA or RNA to produce proteins eliciting appropriate antibodies.

Protection from cryptosporidiosis appears to be due to mucosal B cell immunity which, if absent in AIDS patients, is difficult to establish but, if present, may afford protection against clinical cryptosporidiosis as AIDS progresses. Thus, the invention describes vaccines able to provide active B cell-immunity against cryptosporidiosis in persons at risk for AIDS or in otherwise immunocompromised patients.

IX. DNA and RNA Vaccines

Recently, new approaches appeared which utilize so called DNA or RNA vaccines as described in Science, 259:1745 (1993), hereby incorporated by reference.

DNA or RNA vaccines or native immunity are produced according to the methods described Ibid. Briefly, DNA vectors encoding the deactivated anti-Cryptosporidium antigen DNA or RNA are injected, preferably intramuscularly, wherein said antigen is produced and elicits its own immune responses in the form of a specific anti-Cryptosporidium antigen antibody thereby providing its own immunity and/or cell mediated responses.

UTILITY

The current invention provides means for suitable immunoprotection against Cryptosporidium infections or for a therapeutic use of immune agents produced according to the invention.

Immunotherapy and Prophylaxis

The immunotherapy of cryptosporidiosis in humans and animals may be conducted by administration of the antibodies of the invention to patients with cryptosporidiosis to effectively reduce their symptomatology.

A method for immunotherapeutic treatment, retardation, or inhibition of Cryptosporidium infection comprises administering to a subject in need of such treatment an amount of an anti-Cryptosporidium polyclonal or monoclonal antibody prepared according to the invention, effective to provide immunity against the invasion of Cryptosporidium or effective to inhibit the existing Cryptosporidium infection.

A method of prophylaxis of Cryptosporidium infection comprises administering to a subject in need of such treatment a vaccine comprising the protein or recombinant protein of this invention capable of endogenous development of an inhibitory amount of anti-*Cryptosporidium parvum* antibodies.

Typical immunization is achieved by inoculation of the animal or human host with the antigen protein combined with equal volume of complete Freunds adjuvant at the beginning of the treatments, with the protein plus equal volume of incomplete Freunds adjuvant at week 2, and with protein combined with equal volume of incomplete Freunds adjuvant at week 4.

For passive immunotherapy Cryptosporidium infected hosts, the polypeptide is first combined with appropriate adjuvants and used for the immunization of cows or other donor animals to produce antibodies which may be administered to patients with cryptosporidiosis infection, particularly to AIDS patients, and to other immunocompromised hosts. MAb produced in animals, "humanized" from animal sources, and through chimeric techniques and other derivative techniques may be used for passive immunotherapy.

When in a therapeutic composition, the antigen protein is combined with appropriate adjuvants and used for the immunization of immunocompetent patients who are at risk for cryptosporidiosis either at the time of immunization or in the future. This group includes, but is not restricted to, HIV positive individuals who are still able to respond to vaccination, animal workers, health care workers, day care center children and their caretakers, and children in the developing world.

Formulations suitable for the administration of polypeptides and antibodies such as those described herein are known in the art. Typically, other components stimulatory of immune response may be added as well as fillers, coloring, and the like.

Treatment of Cryptosporidiosis in AIDS Patients and Other Immunocompromised Subjects In AIDS patients *Cryptosporidium parvum* may cause a devastating disease for which there is no treatment. Understanding of the organism and the pathophysiology of the disease it produces, and development of treatment, are very important steps in the treatment of Cryptosporidium infection.

Therefore, the protective activity of proteins of the invention was studied in an in vitro model of Cryptosporidium sporozoite invasion and intracellular development in Madin-Darby Canine Kidney (MDCK) cells. These studies validated the studies performed in the model by correlating inhibition in vitro with protection in an in vivo calf model. The gene for GP900, a sporozoite and merozoite glycoprotein, which is located in micronemes and is accessible to sporozoite surface radioiodination, was identified, cloned and expressed. Similarly, an antigen protein designated as P68 was identified, cloned and expressed. Antibodies raised to fusion proteins expressing portions of the genes (S19, Ag4, S34) inhibited invasion and fusion proteins intracellular development in vitro. Antibodies raised to fusion proteins express portion of the genes (S19-S34) significantly inhibited intracellular development in vivo in a neonatal mouse model.

GP900 and P68 proteins are therefore the first Cryptosporidium vaccine candidates for preparation of active vaccines and passive immune products for human and animal use in combatting Cryptosporidium infections.

Active vaccines and passive immune products prepared from the protein of the invention are suitable for prevention and therapy of *Cryptosporidium parvum* infections in AIDS or other patients suffering from cryptosporidiosis.

Currently, no vaccines or pharmaceuticals are available for the prevention or treatment of cryptosporidiosis. Over 95 drugs have been tested in vitro or in vivo, but, none of these drugs has been shown to be effective. One of the therapeutic approaches for treatment of chronic cryptosporidiosis according to the invention is the use of hyperimmune anti-Cryptosporidium antibodies prepared against the protein antigen of the invention which may be given orally to humans to provide a therapeutic benefit.

As the number of AIDS patients increases, the number of cryptosporidiosis cases will also rise resulting in a critical need for effective therapy and prophylaxis. The current invention provides an effective treatment and prophylaxis against the cryptosporidiosis infection.

EXAMPLE 1

*Cryptosporidium parvum* Parasites

This example illustrates the protocol used for isolation of *Cryptosporidium parvum* parasites.

Oocysts of the Iowa and AUCP-1 isolates of *Cryptosporidium parvum* were passaged through neonatal calves at the Animal Resources Services, University of California, Davis or obtained from a commercial source (Pat Mason) and the oocysts were purified and excysted. The detailed protocol is described in *Infect. Immun.,* 61:4079 (1993).

EXAMPLE 2

Preparation of Murine Anti-Oocyst and Anti-Sporozoite Polyclonal and Monoclonal Antibodies This example describes the procedure used for preparation of murine anti-oocyst and anti-sporozoite polyclonal and monoclonal antibodies.

Polyclonal Antibodies 10 week-old female BALB/c mice were immunized four times intraperitoneally with approximately $5\times10^5$ sonicated *Cryptosporidium parvum* oocysts. The polyclonal antibody fraction of the ascites which was shown to react with the *Cryptosporidium parvum* sporozoite surface, the oocyst surface, and/or with internal antigens of the oocysts, was assessed by an IFA as described in *Infect. Immun.,* 60(12):5132 (1992).

Monoclonal Antibodies

For monoclonal antibody production, mice were immunized intravenously with the supernatant from sonicated *Cryptosporidium parvum* oocysts three days before fusion as described in *J. Immunol.,* 123:1548 (1979) and *J. Parasitol.,* 68:1029 (1982). Hybridoma supernatants were used as the source of antibodies.

Six sporozoite monoclonal antibodies were obtained. The 10C6, 7B3 and E6 monoclonal antibodies were determined to react with GP900. The supernatants of the corresponding hybridoma cultures were used for immunofluorescence assay (IFA) studies and Western blots.

Using the same protocol, infected MDCK cells were used to immunize mice and 3 MAbs to GP900, namely M2, M10, M24 were produced.

EXAMPLE 3

Anti-*Cryptosporidium parvum* Antibodies Eluted from Western Blot

This example describes the procedures used for preparation of antibodies by elution from Western blot.

For SDS-PAGE, $2\times10^9$ oocysts were lysed by 5 cycles of freeze-thawing in 1% Triton Buffer (150 mM Na Cl; 100 mM EDTA; and 1% Triton X-100), in the presence of protease inhibitors: 100 μM E64, 100 μM chymotrypsin, 100 μM pepstatin, and 100 μM leupeptin; and 1.6 mM PMSF, and boiled in sample buffer (SB). Proteins were electrophoresed in 5–15% gradient gels described in Nature, 227:680 (1971) and blotted onto nitrocellulose at 0.7 amperes for 8 hours as described in Inf. Immun., 60(12):5132 (1992). Western blots were incubated with HBC Ig (lot # 40529, obtained from ImmuCell Corporation, Portland, Me.) in dilution 1/500 dissolved in 20 ml PBS for 3 hours at 4° C., rinsed 3 times with phosphate buffered saline (PBS), and the antibodies were eluted with 10 ml of glycine buffer (pH 2.6) for 3 minutes, followed by addition of a 1/10 volume of 2M Tris buffer, pH 8 as described in Inf. Imm., 58:2966 (1990). The eluted antibodies were filter sterilized and concentrated to a final volume of 1 ml in a Centriprep 10 concentrator (Amicon, Mass.).

EXAMPLE 4

Production of Polyclonal Anti-GP900

This example describes the procedure used for preparation of anti-GP900 polyclonal antibodies.

The Triton X-100 (1%) soluble fraction of $2 \times 10^8$ oocysts was immunoprecipitated with MAb 10C6. A>900 kD MW species was identified in gels stained with Coomassie blue in water and excised. Frozen gel containing $2 \times 10^7$ oocyst/sporozoites was pulverized and emulsified in 150 PI of PBS and 150 μl complete Freund's adjuvant (CFA) for intraperitoneal (IP) immunization of mice.

Subsequently, the mice were immunized (IP) three times with the same antigen dissolved in incomplete Freunds adjuvant (ICFA) at approximately 2 week intervals. The anti-GP900 antibody at a dilution of 1:5000 recognized GP900 on Western blots.

EXAMPLE 5

Production of Polyclonal Antibody Against Ag4 and S34 Fusion Proteins

This example describes the procedure used for preparation of the anti-Ag4 and anti-S34 fusion proteins polyclonal antibodies.

Lysogens were produced from the Ag4 and S34 λgt11 clones. Cell lysates and purified protein were made using a protocol and reagents obtained from Promega. Purified fusion protein were emulsified in CFA and injected into rabbits. These injections continued at two week intervals with the substitution of ICFA. Rabbits were sacrificed at the end of 3 months and the antibody was assayed by Western analysis to verify that the antibody recognized a protein >900 kDa.

The β-galactosidase and Ag4-β-galactosidase fusion proteins were purified essentially as described by Promega except that the buffering system used was phosphate buffered saline (PBS) pH 7.4. The purified fusion proteins were then coupled to CNBR sepharose using standard techniques. The antibodies to Ag4-β-galactosidase were depleted by passaging serum over a CNBR sepharose column coupled to β-galactosidase alone- The flow through fraction was applied to a CNBR sepharose column coupled to the purified Ag4 fusion protein. Antibodies directed against the Ag4 portion of the fusion protein were eluted in 0.1 M glycine at a pH of 2.4 and immediately neutralized in 200 μl of 2M Tris, pH 7.4. All affinity purified antibodies reacted with the fusion protein and the respective Cryptosporodium protein but not other E. coli proteins.

S34 was subcloned in GST and coupled to a column CNBR sepharose. Antibodies to S34-β-galactosidase were passed over this column. Antibodies directed against the S34 portion of the fusion protein were eluted in 1M Na thiocyanate and desalted and concentrated.

EXAMPLE 6

Western Analysis

This example describes the Western analysis method used to identify the molecular targets of the protective antibody.

Oocysts ($10^6$ lane) were solubilized in 5% βME (β-mercaptoethanol) containing a sample buffer, resolved by SDS-PAGE and subjected to immunoblotting. Proteins were visualized after incubation with primary antibody with $^{125}$I-labeled Protein A followed by autoradiography or with anti-rabbit IgG conjugated with horseradish peroxidase or alkaline phosphatase followed by calorimetric or chemiluminescent development.

To identify the molecular targets of protective antibody, total Cryptosporidium parvum sporozoite and sporozoite/oocyst proteins were boiled in sample buffer (SB), resolved in 5–15% gradient gels by SDS-PAGE and Western blotted with HBC Ig. In addition, sporozoite/oocyst proteins solubilized in Triton-X 100 were immunoprecipitated with HBC Ig at dilutions 1/1,000; 1/5,000; 1/10,000; 1/50,000 and 1/100,000. Cryptosporidium parvum proteins immunoprecipitated under the same conditions but with SHAM-HBC Ig at dilutions 1/1,000 to 1/10,000 were used as controls. Immunoprecipitates were also resolved by SDS-PAGE and Western blotted. Western blots of HBC Ig immunoprecipitates were developed with HBC Ig (dilution 1:1,000) and SHAM immunoprecipitates were developed with SHAM-HBC Ig (dilution 1:1,000). After incubation with 10 μCi [$^{125}$I]-protein G for 1 hour at room temperature, blots were dried and exposed for autoradiography.

EXAMPLE 7

Southern Hybridization

This example describes the Southern hybridization method used for preparation of hybrids of the invention.

DNA was purified from $1 \times 10^9$ Cryptosporidium parvum oocysts as described in Example 1. DNA was digested with the restriction enzymes according to procedures provided by the manufacturer Promega. Digested DNAs were subjected to electrophoresis in 0.8% agarose gels in 1× TAE or 0.5× TBE. The gel was blotted to a nylon membrane (Hybond N+, Amersham) per manufacturer's instructions. The probe was labeled with $^{32}$P-ATP and hybridized to the membrane by methods known in the art. Results are seen in FIG. 6 where Lanes 1–4 show Iowa isolate DNA and Lane 5 shows AUCP isolate DNA. Lane 1, EcoRI digest; Lane 2, Bgl II digest; Lane 3, Hind III digest; Lanes 4 and 5, Hind I digest.

EXAMPLE 8

Surface Radioiodination and Immunoprecipitation of Cryptosporidium Sporozoite Proteins This example describes the methods used for surface radio-iodination and immunoprecipitation of Cryptosporidium sporozoite proteins.

Oocysts were bleached, excysted and separated from sporozoites prior to iodination of the sporozoite surface and immunoprecipitation of surface proteins as previously described in Infect. Immun. (1993).

A membrane pellet was prepared by centrifuging $1.1 \times 10^7$ sporozoites per ml NETT (0.15 M NaCl, 5 mM EDTA, 0.5 M Tris, 0.5% Triton X-100, pH 7.4) at 100,000×g for 1 hour at 40° C. An aliquot of membrane proteins in 2% SDS 5% p-sample buffer was prepared for total sporozoite surface protein analysis. Aliquots of membrane proteins extracted in 2% SDS were diluted with 9 volumes NETT plus 1% high quality bovine serum albumin (BSA) obtained from Sigma; 1 volume 1% Triton X-100; proteinase inhibitors and either MAb 10C6 or anti-GP900 were added for overnight incubation. Protein A Sepharose 4B beads were added to immobilize the immunoprecipitated proteins. Parasite proteins were solubilized in 2% SDS sample buffer containing β-mercaptoethanol. Samples were boiled 5 minutes and separated by 5–15% gradient SDS-PAGE.

EXAMPLE 9

Immunoelectronmicroscopic Localization of GP900 in *Cryptosporidium parvum*-Infected Rat Intestinal Tissue This example describes the immunoelectronmicroscopic methods used for localization of GP900 antigen in *Cryptosporidium parvum* infected rat intestinal tissue.

Small pieces of terminal ileum were obtained from an immunosuppressed rat experimentally infected with a lamb isolate of the parasite. Tissue samples were fixed with 2% formaldehyde-0.1% glutaraldehyde in PBS for 2 hours at room temperature. They were washed in PBS, dehydrated in ethanol at −20° C., and embedded in LR White obtained from London Resin Co. After polymerization at 37° C. for 5 days, thin sections were cut with a diamond knife and collected on nickel grids coated with formvar. They were floated for 30 minutes on 2.5% nonfat dry milk in PBS (PBSM) and then transferred to anti-GP900 mouse ascites obtained as described in Example 2 and diluted 1:20 in PBSM for 1 hour at room temperature. After the grids were washed in PBS, they were floated on rabbit anti-mouse immunoglobulin serum obtained from Tago, diluted 1:200 in PBSM, for 1 hour at room temperature, and then transferred for 1 hour to 8 nm protein A-coated beads diluted 1:10 in PBSM.

Thin sections were stained with 3% uranyl acetate in water and observed with a Hitachi H600 electron microscope (EM) FIG. 5. EM photographs were also obtained using undiluted MAb IRM hybridoma culture medium and a 1:25 dilution of protein A coated gold beads. Control sections were incubated with unrelated monoclonal and polyclonal antibodies.

EXAMPLE 10

Cloning and Sequencing of a GP900 Locus

This example illustrates the procedure used for cloning and sequencing of a GP900 locus.

The purification and initial characterization of the S34 clone and the description of the restriction fragment genomic expression library from which it was isolated have been described. The Ag4 clone was isolated from the same library as an expression clone which reacted with both the anti-GP900 antibody and MAb IRM. The inserts of the S34 and Ag4 clones were subcloned into BlueScript obtained from Stratagene and sequenced in both directions using Sequenase Version 2.0 DNA Sequencing Kit (UBC) or cycle sequencing (New England Biolabs).

DB8, a 3154 bp insert, which contained the sequences of both S34 and Ag4 was identified by a double of screen of the library using these DNA inserts. PCR amplification products for the ends of DB8 and subsequent clones were used to screen the library to identify new clones which extend the sequence 3' and 5'.

EXAMPLE 11

In Vitro Inhibition of Sporozoite Invasion and Intracellular Development

This example describes the methods used for determination of in vitro inhibition of sporozoite invasion/intracellular development.

Oocysts were used to inoculate confluent Madin Darby Canine Kidney (MDCK) cell monolayers for in vitro inhibition assays of sporozoite invasion and intracellular development as previously described in (*Inf. Immun.*, 61:4079 (1993)) with the following modifications. Chamber slide wells obtained as tissue culture chamber slides from Nunc Inc., Napersville, Ill. containing $10^5$ MDCK cells were overlaid with 400 1 RPMI medium containing $1.5 \times 10^5$ oocysts and antibody or colostrum samples to be tested for inhibitory capacity. Each experimental data point was an average of the number of parasite nuclei counted per 200–300 cell nuclei from each of three independently infected chamber wells. Antisera and controls were used after complement inactivation at 55° C. for five minutes.

Controls included hyperimmune bovine colostrum 40529 Ig (HBC Ig) raised against Cryptosporidium oocysts and sporozoites and SHAM-HBC raised against a herd vaccine at ImmuCell Corp, Portland, Me.

EXAMPLE 12

Dose Response Relationship of Affinity Purified Anti-S34 Antibody and Inhibition of Invasion and Intracellular Development In Vitro This example describes the method used for determination of the dose-response relationship of polyclonal antibodies in vitro with regard to inhibition of sporozoite invasion and intracellular development.

Affinity purified anti-S34 antibody as described in Example 5 was used to determine the dependence of inhibition of invasion/intracellular development on the quantity of antibody added to the in vitro MDCK assay system as described in Example 11. The antibody, at concentrations of 10, 50, 100 and 500 μg/ml in RPMI, was incubated with excysted oocysts on MDCK cell monolayers for two hours. The wells were washed out and refilled with RPMI.

Control wells contained equal amounts of oocysts and RPMI alone, S34-GST at 100 nM, anti-oocyst/sporozoite antibody at a 1:40 dilution and HBC Ig 40529 at a 1:40 dilution. As described in FIG. 9 invasion/intracellular development was reduced to less than 5% of control in the presence of 500 μg/ml and less than 20% in the presence of 100 μg/ml of affinity purified anti-S34 antibody.

EXAMPLE 13

Inhibition of Adhesion by Anti-S34-β-Galactosidase Antibody in the CaCO-2 Adhesion Assay In Vitro This example describes the method used for determination in vitro of the mechanism by which the polyclonal antibody prevents inhibition of sporozoite invasion and intracellular development.

CaCO-2 cells were grown in monolayers and fixed with paraformaldehyde. Sporozoites were isolated, incubated with 1:50 dilutions of anti-β-galactosidase, anti-S-34-β-galactosidase, anti-Ag4-β-galactosidase and HBC Ig 40529 prepared as described in Example 11. Adhesion was determined using an ELISA assay which had previously been validated by correlation with results determined by electron-micrographic assessment of adhesion/inhibition of adhesion.

Anti-S34-β-galactosidase and HBC Ig 40529, the positive control antibody, exhibited an optical density which was 50% of the negative control antibody, anti-β-galactosidase. Anti-AG 4 did not have significant inhibitory activity relative to the control antibody.

EXAMPLE 14

Inhibition of Cryptosporidium Invasion and Intracellular Development in MDCK cells with MAb 10C6

This example describes studies performed to detect inhibition of Cryptosporidium invasion and intracellular development in vitro using monoclonal antibodies.

Cryptosporidium oocysts of the AUCP-1 isolate were excysted and three sporozoite monoclonal antibodies, MAb 10C6, 7B3 and E6, were prepared as described in Example 2. To assess the effect of specific antibodies on sporozoite invasion, MAb 10C6, a monoclonal antibody detecting GP900, was incubated with viable sporozoites for 30 minutes prior to addition to monolayers of MDCK cells.

Sporozoite invasion and intracellular development in MDCK cells was scored at 16 hours after fixation of MDCK cells in formalin and staining with Giemsa. Both invasion and intracellular development were found to be inhibited by >95% compared to the control antibody. Sequential observation of viable, unfixed Cryptosporidium sporozoites by differential phase contrast microscopy after addition of MAb 10C6 revealed initial reactivity of the MAb with the surface followed by shedding of the sporozoite surface coat and production of a tail-like precipitate. At 30 minutes, shedding was complete or sporozoites were immobile and clumped.

In order to determine whether GP900 was shed by the Cryptosporidium sporozoite in the absence of a specific antibody, living sporozoites were allowed to glide on poly-L-lysine coated microscopic slides. Slides were fixed in formalin and GP900 detected by incubation with MAb 7B3 followed by fluorescein labeled anti-mouse second antibody (FIG. 3). MAb 7B3 had previously (data not shown) been shown to detect only one protein, GP900, in sporozoites. In FIG. 3, the sporozoites were shown to be surrounded by GP900 which was shed posteriorly as the sporozoites glided on the poly-L-lysine coated slides. This reaction occurred in the absence of specific antibody which was added only for detection purposes after fixation of the sporozoites and is analogous to the circumsporozoite deposition and localization of the protein of malaria which contains the binding ligand for binding to the hepatocyte adhesion receptor prior to invasion of the hepatocyte.

EXAMPLE 15

Cloning and sequencing of a portion of the P68 locus

This example describes procedures used for cloning and sequencing of a portion of the P68 locus.

The purification and initial characterization of the S19 clone and the description of the restriction fragment genomic expression library from which it was isolated have been described in Example 10. The S19 clone was subcloned into Bluescript and sequenced. The insert was used as a molecular probe to identify further expression library clones which extended 5' and 3'.

When the sequence data generated was added to that derived from S19, a 2380 bp locus was defined. The locus had 1509 bp of open reading frame which remained open at the 5' end.

Comparison of the deduced protein sequence with the Swiss pro data base indicates substantial homology to mechanoenzymes which may be important in the alteration in shape of the cytoskeleton of the parasite and host during the invasion and establishment of intracellular infection.

EXAMPLE 16

In vitro Inhibition of Sporozoite Invasion/ Intracellular Development by Antibody to Recombinant Proteins from the P68 Locus This example illustrates in vitro inhibition of sporozoite invasion and intracellular development by antibody to recombinant proteins isolated from the P68 locus.

S19 was subcloned into the pGEX expression vector to yield the expression clone GST-S19, a recombinant protein fused to glutathione-s-transferase. Antibodies were raised to GST-S19 in 2 rabbits (anti-GST/S19 #1 and anti-GST/S19 #2) and to the native GST in 2 rabbits (anti-GST#1, anti-GST#2). Antibodies were assayed in the same inhibition of invasion assay as the GP900 antibodies, however the graph in FIG. 12 expresses the results as parasites/MDCK cell nucleus rather than as a percentage of the RPMI control. All antibodies were at a dilution of 1:40 except FCS.

The two anti-GST/S19 antibodies inhibited the Cryptosporidium invasion by 46% and 33% relative to control. Both were more inhibitory than an anti-oocyst/ sporozoite antibody made in rabbits. The anti-GST antibodies did not inhibit invasion and intracellular development.

EXAMPLE 17

In Vivo Inhibition of Cryptosporidium Infection in Mice Challenged with Cryptosporidium Oocysts with Anti-S34-β-Galactosidase and Anti-S19-β-Galactosidase Polyclonal Antibodies This example describes the method used for determination of the in vivo inhibition of Cryptosporidium infection of mice challenged with Cryptosporidium oocysts and treated with specific anti-S34-β-galactosidase (FIG. 10) and anti-S19-β-galactosidase (FIG. 13) polyclonal antibodies.

Anti-β-galactosidase,anti-S34-β-galactosidase,anti-Ag4-β-galactosidase and HBC Ig 40529 were tested for inhibitory activity in a neonatal mouse model of Cryptosporidium infection.

Three experiments were performed and the data pooled. In each experiment 5 neonatal mice per group were infected with Cryptosporidium and were fed either 20 μl control PBS, 20 μl of the 3 rabbit antibodies or 20 μl of a 1:5 dilution of HBC Ig 40529 twice a day. A positive pharmacological control substance, 500 mg/kg/d of paromomycin, in dosage approximately 15× the dosage given to human AIDS patients for cryptosporidiosis, was given to mice in 2 experiments. Infection was scored as the mean number of oocysts shed per day during a 5 day collection period.

Anti-GST antibody (1 rabbit) and anti-GST-S19 antibodies (2 rabbits) were made as described in Example 5, except that the fusion protein was glutathione-S-transferase in the pGEX vector. FIG. 13 shows the graphical results of a challenge protection experiment in which antibodies were assayed in vivo in groups of 7 CD1 neonatal mice challenged with $10^4$ oocysts orally on day 6. Oocyst output was scored in Sheather's solution and is expressed as $10^5$/ml. Antisera were diluted 1:2 in 50 mM $NaHCO_3$. The bars are: 1 is preimmune rabbit sera, 2 is anti-GST antibodies, 3 is anti-S19-GST antibodies from rabbit #1, 4 is anti-S19 antibodies from rabbit #2. Inhibition of oocyst excretion relative to control was greater than 45% for the antisera from both rabbits immunized with S19-GST when compared to preimmune sera or antisera to GST alone. When 10 fold more oocysts were used in the challenge the inhibitory effect decreased suggesting that the S19 antibodies titrated a particular molecular event.

EXAMPLE 18

Effect of Specific Cryptosporidium Antigens Mucosal on Lymphocyte Proliferation in Rhesus Macaques Infected with SIV and *Cryptosporidium parvum*

This example describes the methods used for detection of lymphocyte proliferation specific for S34 and S19 in the mucosa of rhesus macaques infected with SIV and *Cryptosporidium parvum*.

Rhesus macaques with SIV infection who were used as vaccine controls, that is they were unvaccinated, in an SIV vaccine trial performed at the California Regional Primate Center at Davis, Calif., were enrolled in a simian AIDS model of a cryptosporidiosis study.

The animals were challenged with whole viable Cryptosporidium oocysts and their clinical state and blood CD4 count were monitored for protracted periods (up to 14 months) before they were sacrificed for evaluation of mucosal lymphocyte responses to Cryptosporidium antigens. The animal's entire GI tract was removed and divided into duodenum/jejunum, ileum and colon segments. The tissues were dissected into small fragments, and intraepithelial mononuclear cells (IELs) were released after incubation of the tissue with DTT and EDTA, collected and purified according to the method described in *Cell. Immun.*, 151:379 (1993).

The remaining tissue was digested with Dispase-collagenase obtained from Boeringer-Mannheim to release lamina propria lymphocytes (LPLs). The mononuclear cells released were collected and purified. MNCs were submitted to fluorescent automatic cell sorting with lymphocyte, and macrophage cell marker antibodies. This method shows that the cells collected by the method of Kang are highly enriched for lymphocytes. Results of these studies are seen in Tables 1 and 2 and are described above in section II.

EXAMPLE 19

Agents Suitable for Passive Immunotherapy

This example describes the preparation of passive immunology agents.

The proteins of the invention bind to antibodies which specifically bind to epitopes of *Cryptosporidium parvum*. These *Cryptosporidium parvum* epitopes are also recognized by B and T cells. The proteins mentioned above are produced in large amounts by reinserting the *Cryptosporidium parvum* DNA from the different clones described in Section I, above, into an expression vector such as pGEX, pET-9d, or baculovirus. The thus constructed hybrid vector is used to transform or transfect a host. The host cells carrying the hybrid vector are then grown in a nutrient medium to allow the production of the gene product.

Vectors pGEX (Pharmacia), disclosed in Gene, 67:31 (1988) or pET-9d (Novagen)/pRSET T7 (Invitrogen) utilize the T7 RNA polymerase and the T7 promoter according to *Meth. Enzymol.*, 185:60 (1990) and hosts derived from *E. coli*. Following protein expression, the vector sequences are easily eliminated so that the subsequent immunogenic protein contains only Cryptosporidium sequences. These expression systems are commercially available and their use is standard in the art.

Recombinant baculovirus is a simple vehicle for the expression of large quantities of protein from eukaryotic or prokaryotic gene origin. The genes are expressed under the control of the Autographa californica multiple nuclear polyhidrosis virus (AcMNPV) polyhedral promoter contained in transfer vectors used to infect *Spodoptera frugiperda* (Sf9 or Sf21) insect cells.

A number of transfer vectors is available for the production of protein from both full length and partial cDNA and genomic clones. Fused or non-fused protein products, depending on the vector used, can produce up to 50% of the total protein in infected cells. The thus obtained recombinant proteins are frequently immunologically and functionally similar to the corresponding endogenous proteins. Proteins with signal peptides may be secreted into the media while those without secretion signals will aggregate in the cells or be localized at the membrane. Baculovirus expression systems are commercially available from Invitrogen.

Thus obtained polypeptide is purified by methods known in the art, and the degree of purification varies with the use of the polypeptide. For use in eliciting polyclonal antibodies, the degree of purity may not need to be high. However, as in some cases impurities may cause adverse reactions, certain degree of purity is preferred and required.

EXAMPLE 20

Agents Suitable for Active Immunotherapy

This example illustrates the agents suitable for active immunotherapy.

Peptides, polypeptides, glycopeptides or proteins comprising epitopes of *Cryptosporidium parvum* recognized by B and/or T cells are produced in large amounts by recloning, as described in Example 19, above. The polypeptide thus obtained are purified as described above. The degree of purification varies with the use of the polypeptides. For use in eliciting polyclonal antibodies, the degree of purity may be lower than for other applications. For the preparation of a pharmaceutical composition, however, the degree of purity must be high, as is known in the art.

When in a therapeutic composition, the polypeptide is combined with appropriate adjuvants and used for the immunization of immunocompetent patients who are at risk for cryptosporidiosis either at the time of immunization or in the future.

This group includes, but is not restricted to, HIV positive individuals who are still able to respond to vaccination, animal workers, health care workers, day care center children and their caretakers, and children in the developing world.

In alternative, the peptides, polypeptides, glycopeptides or proteins of the invention are prepared synthetically using methods known in the art. General methods for synthesizing peptides, polypeptides, glycopeptides or proteins are described in U.S. Pat. No. 5,527, 882, incorporated hereby by reference.

EXAMPLE 21

Preparation of Anti-*Cryptosporidium parvum* Vaccine

This example illustrates procedure for anti-*Cryptosporidium parvum* vaccine.

Vaccine use of recombinant Cryptosporidium antigens.

(1) Antigens: Preferably 10–200 μg of recombinant antigen of the invention, either alone or in combination.

(2) Adjuvant: Any one of a number of adjuvants designed to either:

(a) stimulate mucosal immunity;

(b) target mucosal lymphoid tissue.

Some examples are: liposomes, saponins, lectins, cholera toxin B subunit, *E. coli* labile toxin (LT) B subunit, pluronic block copolymers, hydroxyapatite, plant glucans, acetyl mannan (from Aloe Vera), aluminum hydroxide.

(3) Route of administration: Since the vaccine must stimulate mucosal immunity, it preferably is delivered to a mucosal site. Feasible routes of administration include: oral, nasal, rectal, and vaginal. However, boosting may occur via another route, for example, intramuscular or subcutaneous, or may involve the use of other methods such as foreign DNA which replicates in vivo and dictates protein expression in the host.

(4) Volume: The volume of the vaccine, while not particularly important, should be in the range that would permit ease of use. Preferred range would be 0.5 ml-2.5 ml or so (including adjuvant).

(5) Boost schedule. For non-immunocompromised individuals, the standardly used booster schedule is used.

For immunocompromised individuals, a more aggressive boosting schedule is used. The vaccine is administered to high risk patients initially when their immune status is reasonably good (i.e., CD4 count of >500).

The initial booster is given 1 month after the primary immunization, and again every 3–4 months during progression of the immunodeficient state.

EXAMPLE 22

Polymorphisms in GP900

This example illustrates the method used to prepare mutant and variant products.

Genomic DNA from the Iowa and several other strains was subjected to PCR amplification using primers which were situated outside of domain 2, in the distal region of domain 1 and the proximal region of domain 3. Several prominent bands of different sizes were observed when the PCR products were visualized by ethidium staining of a gel in all of these strains. As a control for tac polymerase, DB8 DNA was also amplified by the polymerase chain reaction. Only a 700 bp amplification product was detected indicating that the multiple bands were a product of amplification of sequences present in the genomic DNA, and were not an artifact of the PCR process.

Two of the amplification products were cloned into sequencing vectors and 4 clones from each of the products were sequenced to determine their relationship to the NINC domain 2 sequence (Table 3). All 8 sequences had an open reading frame indicating that they were portions of DNA which could be the blueprint for a GP900 protein. All 8 sequences appeared to have in-frame (multiples of 3) DNA deletions with respect to the NINC sequence. All 8 coded for a domain 2 which had conservation of the threonine rich regions, but all 8 differed from each other. The DNA data indicate that mutation in domain 8 is common. The conservation of threonines and the in-frame nature of all 8 clones indicate that there are selection pressures acting at the level of the protein (presumably production of an attachment protein which will mediate attachment and allow for invasion and propagation) which determine which genotypic variants are maintained in a strain. Results show that there are mutants of GP900 which are maintained in an isolate's gene pool, presumably as variant alleles at a single locus in haploid stages of the organism.

SEQUENCE LISTING

<160> NUMBER OF SEQ ID NOS: 15

<210> SEQ ID NO 1
<211> LENGTH: 5163
<212> TYPE: DNA
<213> ORGANISM: Cryptosporidium parvum

<400> SEQUENCE: 1

```
aattttggaa ggttcaattg caggtattag aagcgaatct tgcattgtat ctgaactgaa      60
ctttacatct actactggat ttacaacgga cacatcaatg aattggccgg taagtatcac     120
aagtggtgaa ctgaaggatc caaacaaaca agctactatt tctggttcaa gatcttgtgg     180
atggaaacaa ggttatagca ttgattcatc caccgggttt agagttgatt ctatcactgg     240
tctcccaact gatccatact ctaattgtcc attcaaccct gtcactggaa atttagtcag     300
taggtccact ggtaaaacta ttccaaacac ttatgcaggt gtttatcgtt ctaatgagac     360
taagaccact gagcctagtg caaacactta tgcaggtgtt tatcgttcta atgagactaa     420
gaccactgag cctagtgcaa acaccaactt cttgttggta gatcctaaga ttaatgctcc     480
ttgtaattct gagaactctt ttgaacaagg tcaaatattt gatatgggca gtaaggtata     540
```

```
cattccatac actaaatgtg ttggagtgaa acacacaaca acaacaacaa caactactac       600
tactactact acgacaacaa caacaacaac gacaacaaca acaactacta caactactac       660
cactactact acgacaacaa caacaacaac aacaacaaca acaacaacaa caacaacaac       720
aacaacaaca acaacgacta ctactactac tactactact actactacta ctactactac       780
aaccacaaca actacaacca caactacaac cacaacaact acaaccacaa caacaacaac       840
cacaacaact acaaccacaa ctacaaccac aacaactaca accacaacaa ccacaaccac       900
aaccacaact accaagaaac caacaacaac aactacaaca acaacaacaa caacaacaac       960
tactactaca accaccacaa caacaacaac aacaacaact acaactacca agaaaccaac      1020
aactactact actactacca caacaacaac aactactact actaccacaa caacaacaac      1080
tactactact actacaacaa caacaacaac aacaacaaca acaacaacta ccacgaaacc      1140
aacaacaaca acaacaacta ctactactac tacaaccaag aaaccaacaa caactaccac      1200
tgccacaaca acaactacta cttctgaaac tgagagtgta attaaacctg atgaatggtg      1260
ttggttggaa aagaatggcg aatgtgaggc aaaaggagca acttatgttg gtgttatcgg      1320
aaaagatgga cgtattgaaa atggaatggc atttacaatg attccaaatg atgacacgca      1380
tgtccgcttc agatttaagg ttaaagatgt agggaacact atttcagtaa gatgcagaaa      1440
aggtgcaggt aaactcgagt tcccagatag aagtttggat ttcacaattc ctccagtagc      1500 tggcctataac agctgttcaa taatagttgg tgtgagcggc gatggaaaaa ttcacgtaag      1560
cccatacggt tctaaggatg tctctctaat aagtgctcca atacaacctt ctgagttatt      1620
caatgaagtt tattgcgaca cttgtactgc gaagtatggt gcattcactc tggatatcaa      1680
acttcagctg atttcgtaac aacgactacc gcaaaaccaa caactactac aactggagcc      1740
ccaggacaac caacaactac tacaactgga agtccaagca aaccaactac tactaccact      1800
actaaggcaa caacaaccac aacaactctt aatccaatca ttacaacaac aactcaaaaa      1860
ccaacaacaa caacaacaac aaaggttcca ggtaagccac caatagccac aacaacaaca      1920
acattaaagc caatagttac aacaacaaca acaaaagcaa caacaacaac aacaacaaca      1980
gtgccaacga caactactac taccaagaga gacgaaatga caacaacaac gacaccatta      2040
cctgatatcg gtgacattga aattacacca atcccaattg aaaagatgtt ggataagtac      2100
acaagaatga tttatgacta taacagtggt ttattattag actctaatga tgaaccaatt      2160
ccaggttctc aagcaggaca aatagctgat acaagcaatt tattcccagt tcaaactcac      2220
aagagtactg gtttaccaat tgatccaatg gttggtcttc catttgatcc aaaatcaggt      2280
aatttagtac atccatatac caatcaaaca atgtctggtt tatcggtatc atatcttgct      2340
gctaagaatt tgacagttga tactgatgaa acctacggtt taccaattga tacactcact      2400
ggttacccat tggatccagt cagtttgatt ccgttcaatc cagaaactgg tgaattgttt      2460
gatccaatat cagatgagat aatgaatgga acaattgcag gtattgtttc aggaatttct      2520
gcaagtgagt cattattatc tcagaaatca gctctaatcg acccagcaac aaatatggtt      2580
gttggagaat tggtggatt gttgaaccca gcaacaggag tgatgattcc aggttttttta      2640 ggtccatcag agcaaactca attctcccct gagattgaag atggtggtat tattcctcca      2700
gaagtagcag cagcaaatgc tgataaattc aagttatcta ttcctccaag cgtaccagaa      2760
tcaattccag aaaaggatca gaagattgat tctatttctg aattgatgta tgatattgag      2820
tcaggtagac ttattggtca agtatcaaag agaccaatcc caggttcaat tgctggtgac      2880
ttgaacccaa taatgaagac accaacacaa actgacagtg taactggtaa accaatcgat      2940
```

```
ccaaccacag gtctgccttt caatccacca actggtcatt tgattaaccc aacaaataat      3000 ataccatgg attcttcatt tgctggtgca tacaaatatg cagtttcaaa tggtattaag       3060
actgataatg tttatggttt accagttggt gaaataacag gtttaccaaa ggatccaggc      3120
tcagatattc catttaactc aactacaggt gaattagttg atccatcaac aggaaagcca     3180
attaacaatt ctactgctgg tattgttagt ggaaaacctg gcttaccacc tattgaagat      3240
gaaaatggta atttgtttga tccatcaact aacttgccaa tagatggtaa taaccaatta     3300
gttaacccag aaaccaacag cactgtctca ggatcaactt caggtactac aaaaccaaaa     3360
ccaggaattc cagtcaatgg tggaggtgtt gtacctgatg aagaagctaa agatcaagcc     3420
gataagggta aggatggatt aattgttcca ccaactaatt ctatcaataa agatccagta     3480
acaaatactc agtacagtaa tactactggt aacattatta acccagaaac aggaaaagtt    3540
attccaggtt cacttccagg ctctctcaac tatccatcat tcaatactcc acaacaaact     3600
gatgagatta caggaaagcc agttgatact gttactggtt tgccatatga tccatctaca   3660
ggtgaaatta tcgatcctgc aactaaatta ccaattccag gatcagttgc aggtgatgaa    3720
atcctcactg aagtattgaa cattacaaca gatgaagtaa caggtttgcc aattgatctt    3780
gaaactggtc ttccaagaga tccagtatca ggactcccac aacttccaaa tggtaccttg    3840
gttgatccat caaataaaaa accaattcca ggttcacatt ccggatttat taatggtaca    3900
tctggagaac aatcacatga gaaagatcca agtactggta agccacttga tccaaataca    3960
ggtttgcacc cattcgatga agattcaggt agtttaatta acccagagac tggagataaa    4020
cttcaaggat cacattctgg tacatttatg ccagtaccag gtaaaccaca aggtgaaaat    4080
ggaggtatca tgacacctga gcagatattg gaagcattaa ataaattgcc aacaagtaat    4140
gaagtaaata tttcaccaag accaagttca gatgctgttc cagatagacc aacaaatact    4200
tggtggaata agatttctgg tcaaacctac caggttgatg gaaagaagac tatcctaggt    4260
tctgcagctt cagtaattca cactgctctt ggaacaccaa ctcaaactga tccaacaaca   4320
ggacttccat ctgatccatc aacaggttta ccattcattc caggatttaa cgtgcttgta   4380
gatcctcaga ctggagagca aatcaagggt tctgttcctt atgtttcatt gtacgttaag   4440
gaaaagaata ttgtaacaga agctgcttat ggtctaccag ttgatccaaa gactggtttc   4500
ccaattgatc caattagtta cctcccgttt gctaagaatg gcgaactaat tgatcctatc    4560
tctggtaaat atttcagtgg ttcaattgct ggattcattt ctggtaaagc tggttcacaa    4620
tctaaatcat ctgatgaatc aggtaatcca attgatccat caacaaatat gccttacgat   4680
ccaaaaggcg gcaaattaat tgatccgaaa tctggcattg ctattgataa ttctgttcca   4740
ggtgtgtttg caactgtacc tggtactgct gcaccgaaaa agggtggtgt cattccggag    4800
tcagttgcag ctgaggcagc aaagaaatac tttgcagcca atgttgaggg agagggagaa    4860
ggagaagaag ttccaccacc gccagaatca tctagtaaca ttgcaatcca agctgctggt    4920
ggtgcttctg ctgctgtagg tctcgtagct gctgttggtg catggtatgc aagcagaaac    4980
agacaggaag gagaagatga tgatgactat cagatggatt tgaagcagaa tatgaagaag   5040
aagaggaaga gaggggtgat gaagcagcaa atgaaactgt tgttacaatt gagcgtgatt    5100
catcattctg gaacgaatct taaacgtaga aaagattttt ccaattcaaa aaaatttcga   5160
ata                                                                  5163

<210> SEQ ID NO 2
<211> LENGTH: 5318
```

<212> TYPE: DNA
<213> ORGANISM: Cryptosporidium parvum

<400> SEQUENCE: 2

```
aattttggaa ggttcaattg caggtattag aagcgaatct tgcattgtat ctgaactgaa      60
ctttacatct actactggat ttacaacgga cacatcaatg aattggccgg taagtatcac     120
aagtggtgaa cgtaaggatc caaacaaaca agctactatt tctggttcaa gatcttgtgg     180
atggaaacaa ggttatagca ttgattcatc caccgggttt agagttgatt ctatcactgg     240
tctcccaact gatccatact ctaattgtcc attcaaccct gtcactgaa attta gtcag      300
taggtccact ggtaaaacta ttccaaacac ttatgcaggt gtttatcgtt ctaatgagac     360
taagaccact gagcctagtg caaacactta tgcaggtgtt tatcgttcta atgagactaa     420
gaccactgag cctagtgcaa acaccaactt cttgttggta gatcctaaga ttaatgctcc     480
ttgtaattct gagaactctt tgaacaagg tcaaatattt gatatgggca gtaaggtata      540
cattccatac actaaatgtg ttggagtgaa acacacaaca acaacaacaa caactactac     600
tactactact acgacaacaa caacaacaac gacaacaaca caactactaca actactac     660
cactactact acgacaacaa caacaacaac aacaacaaca acaacaacaa caacaacaac     720
aacaacaaca acaacgacta ctactactac tactactact actactacta ctactactac     780
aaccacaaca actacaacca caactacaac cacaacaact caaccacaa caacaacaac     840
cacaacaact acaccacaa ctacaaccac aacaactaca accacaacaa ccacaaccac      900
aaccacaact accaagaaac caacaacaac aactacaaca acaacaacaa caacaacaac     960
tactactaca accaccacaa caacaacaac aacaacaact acaactacca agaaaccaac    1020
aactactact actactacca caacaacaac aactactact actaccacaa caacaacaac    1080
tactactact actacaacaa caacaacaac aacaacaaca acaacaacta ccacgaaacc    1140
aacaacaaca acaacaacta ctactactac tacaaccaag aaaccaacaa caactaccac    1200
tgccacaaca acaactacta cttctgaaac tgagagtgta attaaacctg atgaatggtg    1260
ttggttggaa aagaatggcg aatgtgaggc aaaaggagca acttatgttg gtgttatcgg    1320
aaaagatgga cgtattgaaa atggaatggc atttacaatg attccaaatg atgacacgca    1380
tgtccgcttc agatttaagg ttaaagatgt agggaacact atttcagtaa gatgcagaaa    1440
aggtgcaggt aaactcgagt tcccagatag aagtttggat ttcacaattc ctccagtagc    1500
tggccataac agctgttcaa taatagttgg tgtgagcggc gatggaaaaa ttcacgtaag    1560
cccatacggt tctaaggatg tctctctaat aagtgctcca atacaacctt ctgagttatt    1620
caatgaagtt tattgcgaca cttgtactgc gaagtatggt gcattcactc tggatatcaa    1680
acttcagctg atttcgtaac aacgactacc gcaaaccaa caactactac aactggagcc     1740
ccaggacaac caacaactac tacaactgga agtccaagca aaccaactac tactaccact    1800
actaaggcaa caacaaccac aacaactctt aatccaatca ttacaacaac aactcaaaaa    1860
ccaacaacaa caacaacaac aaaggttcca ggtaagccac aatagccac aacaacaaca     1920
acattaaagc caatagttac aacaacaaca caaaagcaa caacaacaac aacaacaaca    1980
gtgccaacga caactactac taccaagaga acgaaatga caacaacaac gacaccatta    2040
cctgatatcg gtgacattga aattacacca atcccaattg aaaagatgtt ggataagtac    2100
acaagaatga tttatgacta taacagtggt ttattattag actctaatga tgaaccaatt    2160
ccaggttctc aagcaggaca aatagctgat acaagcaatt tattcccagt tcaaactcac    2220
aagagtactg gtttaccaat tgatccaatg gttggtcttc catttgatcc aaaatcaggt    2280
```

```
aatttagtac atccatatac caatcaaaca atgtctggtt tatcggtatc atatcttgct    2340
gctaagaatt tgacagttga tactgatgaa acctacggtt taccaattga tacactcact    2400
ggttacccat tggatccagt cagtttgatt ccgttcaatc cagaaactgg tgaattgttt    2460
gatccaatat cagatgagat aatgaatgga acaattgcag gtattgtttc aggaatttct    2520
gcaagtgagt cattattatc tcagaaatca gctctaatcg acccagcaac aaatatggtt    2580
gttggagaat tggtggatt gttgaaccca gcaacaggag tgatgattcc aggttttta    2640 ggtccatcag agcaaactca attctcccct gagattgaag atggtggtat tattcctcca    2700
gaagtagcag cagcaaatgc tgataaattc aagttatcta ttcctccaag cgtaccagaa    2760
tcaattccag aaaaggatca gaagattgat tctatttctg aattgatgta tgatattgag    2820
tcaggtagac ttattggtca agtatcaaag agaccaatcc caggttcaat tgctggtgac    2880
ttgaacccaa taatgaagac accaacacaa actgacagtg taactggtaa accaatcgat    2940
ccaaccacag gtctgccttt caatccacca actggtcatt tgattaaccc aacaaataat    3000
aataccatgg attcttcatt tgctggtgca tacaaatatg cagtttcaaa tggtattaag    3060
actgataatg tttatggttt accagttggt gaaataacag gtttaccaaa ggatccaggc    3120
tcagatattc catttaactc aactacaggt gaattagttg atccatcaac aggaaagcca    3180
attaacaatt ctactgctgg tattgttagt ggaaaacctg gcttaccacc tattgaagat    3240
gaaaatggta atttgtttga tccatcaact aacttgccaa tagatggtaa taaccaatta    3300
gttaacccag aaaccaacag cactgtctca ggatcaactt caggtactac aaaaccaaaa    3360
ccaggaattc cagtcaatgg tggaggtgtt gtacctgatg aagaagctaa agatcaagcc    3420
gataagggta aggatggatt aattgttcca ccaactaatt ctatcaataa agatccagta    3480
acaaatactc agtacagtaa tactactggt aacattatta acccagaaac aggaaaagtt    3540
attccaggtt cacttccagg ctctctcaac tatccatcat tcaatactcc acaacaaact    3600
gatgagatta caggaaagcc agttgatact gttactggtt tgccatatga tccatctaca    3660
ggtgaaatta tcgatcctgc aactaaatta ccaattccag gatcagttgc aggtgatgaa    3720
atcctcactg aagtattgaa cattacaaca gatgaagtaa caggtttgcc aattgatctt    3780
gaaactggtc ttccaagaga tccagtatca ggactcccac aacttccaaa tggtaccttg    3840
gttgatccat caaataaaaa accaattcca ggttcacatt ccggatttat taatggtaca    3900
tctggagaac aatcacatga gaaagatcca agtactggta agccacttga tccaaataca    3960
ggtttgcacc cattcgatga agattcaggt agtttaatta acccagagac tggagataaa    4020
cttcaaggat cacattctgg tacatttatg ccagtaccag gtaaaccaca aggtgaaaat    4080
ggaggtatca tgacacctga gcagatattg gaagcattaa ataaattgcc aacaagtaat    4140
gaagtaaata tttcaccaag accaagttca gatgctgttc cagatagacc aacaaatact    4200
tggtggaata agatttctgg tcaaacctac caggttgatg gaaagaagac tatcctaggt    4260
tctgcagctt cagtaattca cactgctctt ggaacaccaa ctcaaactga tccaacaaca    4320
ggacttccat ctgatccatc aacaggttta ccattcattc caggatttaa cgtgcttgta    4380
gatcctcaga ctggagagca aatcaagggt tctgttcctt atgttcatt gtacgttaag    4440 gaaaagaata ttgtaacaga agctgcttat ggtctaccag ttgatccaaa gactggtttc    4500
ccaattgatc caattagtta cctcccgttt gctaagaatg gcgaactaat tgatcctatc    4560
tctggtaaat atttcagtgg ttcaattgct ggattcattt ctggtaaagc tggttcacaa    4620
tctaaatcat ctgatgaatc aggtaatcca attgatccat caacaaatat gccttacgat    4680
```

-continued

```
ccaaaaggcg gcaaattaat tgatccagaa tctggcattg ctattgataa ttctgtttca    4740
ggtgtgtttg caactgtacc tggtactgct gcaccgaaaa agggtggtgt cattccggag    4800
tcagttgcag ctgaggcagc aaagaaatac tttgcagcca atgttgaggg agagggagaa    4860
ggagaagaag ttccaccacc gccagaatca tctagtaaca ttgcaatcca agctgctggt    4920
ggtgcttctg ctgctgtagg tctcgtagct gctgttggtg catggtatgc aagcagaaac    4980
agacaggaag gagaagatga tgatgactat cagatggatt tgaagcagaa tatgaagaag    5040
aagaggaaga gagggtgat gaagcagcaa atgaaactgt tgttacaatt gagcgtgatt     5100
catcattctg gaacgaatct taaacgtaga aaagatttt ccaattcaaa aaaatttcga     5160
atatgaaaat taatgatttc ctaatatcaa atattactac atttctacat ttcctattga    5220
aatatacgat ttactaacat attgctaatt aataaatgat taataatgac aaaattcaac    5280
gatatgatga atctatcaaa gcgtttcaaa tggagaaa                            5318
```

<210> SEQ ID NO 3
<211> LENGTH: 1509
<212> TYPE: DNA
<213> ORGANISM: Cryptosporidium parvum

<400> SEQUENCE: 3

```
agtaagggtc aattatttaa cccagtaagt aagttgtgtg tacgacttaa agacaatgtt     60
gtaggtggag gagctctggt tttggatgat tgtcgtaaag ctagtgatgg aagtggatta    120
ttcgaattaa tgccaaacaa tcagctcaga ttagctagag gtggaaatct atgcttaaca    180
agtccaggag ataagccagg agtcgcgaat gttgcattaa actcagcagc cagttccaca    240
agtgtggtta gaacaggtat tgagaatggt ccagcaatgc ctgttgatgg aaaggataca    300
tcatattggt tgtcagattc ttcaactcct ggtaaagatt ctgcaaatgt taactttttg    360
agtgataccg gttcagttac aaaacttaaa gatatcttta ttgagtggaa atatcctgcc    420
attgacttta atattgattt aagtgaaaat ggaaaggaat atcaaaccca gttctctgtg    480
aataataatg gattaatgtc aaccacttat tcattgaaag gaaagaaagc aagatatgtc    540
aaaattcaaa tgacaattcc aagccaagat gagacaggga aatatgtgta tggtatcaaa    600
caggtgagaa tattcagtaa tactatgaga agtactgttg aggattgtag tagtgttaaa    660
caacataatg atggtagaga caaaatattc ccactcccat ataatggtga taattttgca    720
cccggattat tgttaaaggc tcacggaatt agtgtaaaga atagattaaa tgaattacaa    780
gagctttctg gtaaggtaac ttcaatatta ccaaatttgg atgcatgtag aaagacttct    840
gatggaagag ataacacatt aaagatgcag gcaaccaaat taggattttt gtcagaaaaa    900
ttggagaaat taacttccga ctataatctc gagtataagt ttacgaagcc agctttagga    960
ggttccgagt tatatccagg ggaagattgt gttgctatta agaatgataa gactcaggaa    1020
gccattagtg gttttttatta tgttagacca ttctgttcaa ccaaaccatt gagagtttac    1080
tgtgatatga acactggaaa tacaatctat ccaatgaaa tgagtgttca ttcttccaga    1140
gcagcttctt cagcatgtgc aactgttgga ttaaaaccat tattgttaag ggacaaaaag    1200
gaatctgttg taggtattaa gaagatgttg aaatatgatga atattaatga aatagaaga    1260 gttattcctt tgactcacga ctttggttgt gataatccta aaggatgcaa ttcacaattt    1320
acacagttag gcagtggtgt tgaagaattt gttgctgcat ctcctcaggc agcagcttca    1380
aactctacat ctggagcact tccagaactg gttctttgca gtacaaatac caatttgaag    1440
catgaaagca atgcaatttc cttgtcttgt gaaagcagat tctctgatat gaaggtattt    1500
```

-continued

```
catttggat                                                              1509

<210> SEQ ID NO 4
<211> LENGTH: 2380
<212> TYPE: DNA
<213> ORGANISM: Cryptosporidium parvum

<400> SEQUENCE: 4
agtaagggtc aattatttaa cccagtaagt aagttgtgtg tacgacttaa agacaatgtt     60
gtaggtggag gagctctggt tttggatgat tgtcgtaaag ctagtgatgg aagtggatta    120
ttcgaattaa tgccaaacaa tcagctcaga ttagctagag gtggaaatct atgcttaaca    180
agtccaggag ataagccagg agtcgcgaat gttgcattaa actcagcagc cagttccaca    240
agtgtggtta gaacaggtat tgagaatggt ccagcaatgg ctgttgatgg aaaggataca    300
tcatattggt tgtcagattc ttcaactcct ggtaaagatt ctgcaaatgt taactttttg    360
agtgataccg gttcagttac aaaacttaaa gatatcttta ttgagtggaa atatcctgcc    420
attgacttta atattgattt aagtgaaaat ggaaaggaat atcaaaccca agtttctgtg    480
aataataatg gattaatgtc aaccacttat tcattagaag gaaagaaagc aagatatgtc    540
aaaattcaaa tgacaattcc aagccaagat gagacaggga aatatgtgta tggtatcaaa    600
caggtgagaa tattcagtaa tactatgaga agtactgttg aggattgtag tagtgttaaa    660
caacataatg atggtagaga caaaatattc ccactcccat ataatggtga taattttgca    720
cccggattat tgttaaaggc tcacggaatt agtgtaaaga atagattaaa tgaattacaa    780
gagctttctg gtaaggtaac ttcaatatta ccaaatttgg atgcatgtag aaagacttct    840
gatggaagag ataacacatt aaagatgcag gcaaccaaat taggattttt gtcagaaaaa    900
ttggagaaat taacttccga ctataatctc gagtataagt ttacgaagcc agctttagga    960
ggttccgagt tatatccagg ggaagattgt gttgctatta agaatgataa gactcaggaa   1020
gccattagtg gttttttatta tgttagacca ttctgttcaa ccaaaccatt gagagtttac   1080
tgtgatatga acactggaaa tacaatctat ccaatgaaa tgagtgttca ttcttccaga    1140
gcagcttctt cagcatgtgc aactgttgga ttaaaaccat tattgttaag ggacaaaaag   1200
gaatctgttg taggtattaa gaagatgttg aatatgatga atattaatga taatagaaga   1260
gttattcctt tgactcacga ctttggttgt gataatccta aaggatgcaa ttcacaattt   1320
acacagttag gcagtggtgt tgaagaattt gttgctgcat ctcctcaggc agcagcttca   1380
aactctacat ctggagcact tccagaactg gttctttgca gtacaaatac caatttgaag   1440
catgaaagca atgcaatttc cttgtcttgt gaaagcagat tctctgatat gaaggtattt   1500
catttggatt agtaacctga attaaatgat gtagaagaga tctaatagct ttagtatgtt   1560
gcaaaaattc gttagaaagt tcaaggaact caagcttaaa cttcttgtt ttctttctcc     1620 atgatttttt cttgttatac ttctctgcaa ccctaagtgt ttcttgccca aaattgatta   1680
attctctgat cttgggccta tatttggtga actcattaat aaatgtttca gtaacgacac   1740
tatttgggtt ttctgttaaa tctagtccaa agttaacagt tttgatcttc tttgccttat   1800
tataacaaac attaatctcc ttttcttgtt caggagatag ttcaacgtct tttgagtatg   1860
aaatacttgc ttctttatta taattcggat attcgctttg atcagtttgg ccttctgatc   1920
cgtcaatttg tgatctacgt tctataatag cttctggaat atctgtagca ggagcatctt   1980
gcggctttaa tccaacagga agctccttta ctgtattaat ataggagaac ggcatatttc   2040
caaagccatt agtatttaat tcgccattat tctgagtacc cttgggagaa ttatcgctaa   2100
```

-continued

```
tagaatcccc ttcagccttt tgaaggttga aattcagctg agtttcatcc atactacttg    2160
gatcagaatc ttcaaatcca gtagctagtc ttctagagaa agactcagca tcactatatc    2220
cttcattagt tgtttcctca gattctagaa tcttctccgt gatactttca gtaggatttg    2280
atgcgcgtaa atacagggct ttcctgcttg ttgaaatggc cagtttctgt aatttgagtt    2340
ttttcctcac tttcagactg ttctggataa tccggaattt                          2380
```

<210> SEQ ID NO 5
<211> LENGTH: 1721
<212> TYPE: PRT
<213> ORGANISM: Cryptosporidium parvum

<400> SEQUENCE: 5

```
Ile Leu Glu Gly Ser Ile Ala Gly Ile Arg Ser Glu Ser Cys Ile Val
  1               5                  10                  15

Ser Glu Leu Asn Phe Thr Ser Thr Thr Gly Phe Thr Thr Asp Thr Ser
                 20                  25                  30

Met Asn Trp Pro Val Ser Ile Thr Ser Gly Glu Arg Lys Asp Pro Asn
             35                  40                  45

Lys Gln Ala Thr Ile Ser Gly Ser Arg Ser Cys Gly Trp Lys Gln Gly
         50                  55                  60

Tyr Ser Ile Asp Ser Ser Thr Gly Phe Arg Val Asp Ser Ile Thr Gly
 65                  70                  75                  80

Leu Pro Thr Asp Pro Tyr Ser Asn Cys Pro Phe Asn Pro Val Thr Gly
                 85                  90                  95

Asn Leu Val Ser Arg Ser Thr Gly Lys Thr Ile Pro Asn Thr Tyr Ala
            100                 105                 110

Gly Val Tyr Arg Ser Asn Glu Thr Lys Thr Thr Glu Pro Ser Ala Asn
            115                 120                 125

Thr Tyr Ala Gly Val Tyr Arg Ser Asn Glu Thr Lys Thr Thr Glu Pro
        130                 135                 140

Ser Ala Asn Thr Asn Phe Leu Leu Val Asp Pro Lys Ile Asn Ala Pro
145                 150                 155                 160

Cys Asn Ser Glu Asn Ser Phe Glu Gln Gly Gln Ile Phe Asp Met Gly
                165                 170                 175

Ser Lys Val Tyr Ile Pro Tyr Lys Cys Val Gly Val Lys His Thr
            180                 185                 190

Thr Thr Thr Thr Thr Thr Thr Thr Thr Thr Thr Thr Thr Thr Thr
            195                 200                 205

Thr Thr Thr Thr Thr Thr Thr Thr Thr Thr Thr Thr Thr Thr Thr
        210                 215                 220

Thr Thr Thr Thr Thr Thr Thr Thr Thr Thr Thr Thr Thr Thr Thr Thr
225                 230                 235                 240

Thr Thr Thr Thr Thr Thr Thr Thr Thr Thr Thr Thr Thr Thr Thr
            245                 250                 255

Thr Thr Thr Thr Thr Thr Thr Thr Thr Thr Thr Thr Thr Thr Thr
        260                 265                 270

Thr Thr Thr Thr Thr Thr Thr Thr Thr Thr Thr Thr Thr Thr Thr
            275                 280                 285

Thr Thr Thr Thr Thr Thr Thr Thr Thr Thr Thr Thr Thr Thr Thr
        290                 295                 300

Lys Lys Pro Thr Thr Thr Thr Thr Thr Thr Thr Thr Thr Thr Thr Thr
305                 310                 315                 320

Thr Thr Thr Thr Thr Thr Thr Thr Thr Thr Thr Thr Thr Thr Thr
```

-continued

```
                325                 330                 335
Lys Lys Pro Thr Thr Thr Thr Thr Thr Thr Thr Thr Thr Thr
            340                 345                 350
Thr Thr Thr Thr Thr Thr Thr Thr Thr Thr Thr Thr Thr Thr
            355                 360                 365
Thr Thr Thr Thr Thr Thr Thr Thr Thr Thr Lys Pro Thr Thr Thr Thr
            370                 375                 380
Thr Thr Thr Thr Thr Thr Thr Thr Thr Lys Lys Pro Thr Thr Thr Thr Thr
385                 390                 395                 400
Ala Thr Thr Thr Thr Thr Thr Ser Glu Thr Glu Ser Val Ile Lys Pro
            405                 410                 415
Asp Glu Trp Cys Trp Leu Glu Lys Asn Gly Glu Cys Glu Ala Lys Gly
            420                 425                 430
Ala Thr Tyr Val Gly Val Ile Gly Lys Asp Gly Arg Ile Glu Asn Gly
            435                 440                 445
Met Ala Phe Thr Met Ile Pro Asn Asp Asp Thr His Val Arg Phe Arg
            450                 455                 460
Phe Lys Val Lys Asp Val Gly Asn Thr Ile Ser Val Arg Cys Arg Lys
465                 470                 475                 480
Gly Ala Gly Lys Leu Glu Phe Pro Asp Arg Ser Leu Asp Phe Thr Ile
            485                 490                 495
Pro Pro Val Ala Gly His Asn Ser Cys Ser Ile Ile Val Gly Val Ser
            500                 505                 510
Gly Asp Gly Lys Ile His Val Ser Pro Tyr Gly Ser Lys Asp Val Ser
            515                 520                 525
Leu Ile Ser Ala Pro Ile Gln Pro Ser Glu Leu Phe Asn Glu Val Tyr
            530                 535                 540
Cys Asp Thr Cys Thr Ala Lys Tyr Gly Ala Ile His Ser Gly Tyr Gln
545                 550                 555                 560
Thr Ser Ala Asp Phe Val Thr Thr Thr Ala Lys Pro Thr Thr Thr
            565                 570                 575
Thr Thr Gly Ala Pro Gly Gln Pro Thr Thr Thr Thr Gly Ser Pro
            580                 585                 590
Ser Lys Pro Thr Thr Thr Thr Thr Lys Ala Thr Thr Thr Thr
            595                 600                 605
Thr Leu Asn Pro Ile Ile Thr Thr Thr Gln Lys Pro Thr Thr Thr
            610                 615                 620
Thr Thr Lys Val Pro Gly Lys Pro Pro Ile Ala Thr Thr Thr Thr
625                 630                 635                 640
Thr Leu Lys Pro Ile Val Thr Thr Thr Thr Lys Ala Thr Thr Thr
            645                 650                 655
Thr Thr Thr Thr Val Pro Thr Thr Thr Thr Thr Lys Arg Asp Glu
            660                 665                 670
Met Thr Thr Thr Thr Thr Pro Leu Pro Asp Ile Gly Asp Ile Glu Ile
            675                 680                 685
Thr Pro Ile Pro Ile Glu Lys Met Leu Asp Lys Tyr Thr Arg Met Ile
            690                 695                 700
Tyr Asp Tyr Asn Ser Gly Leu Leu Leu Asp Ser Asn Asp Glu Pro Ile
705                 710                 715                 720
Pro Gly Ser Gln Ala Gly Gln Ile Ala Asp Thr Ser Asn Leu Phe Pro
            725                 730                 735
Val Gln Thr His Lys Ser Thr Gly Leu Pro Ile Asp Pro Met Val Gly
            740                 745                 750
```

-continued

```
Leu Pro Phe Asp Pro Lys Ser Gly Asn Leu Val His Pro Tyr Thr Asn
        755                 760                 765
Gln Thr Met Ser Gly Leu Ser Val Ser Tyr Leu Ala Ala Lys Asn Leu
        770                 775                 780
Thr Val Asp Thr Asp Glu Thr Tyr Gly Leu Pro Ile Asp Thr Leu Thr
785                 790                 795                 800
Gly Tyr Pro Leu Asp Pro Val Ser Leu Ile Pro Phe Asn Pro Glu Thr
                805                 810                 815
Gly Glu Leu Phe Asp Pro Ile Ser Asp Glu Ile Met Asn Gly Thr Ile
                820                 825                 830
Ala Gly Ile Val Ser Gly Ile Ser Ala Ser Glu Ser Leu Leu Ser Gln
                835                 840                 845
Lys Ser Ala Leu Ile Asp Pro Ala Thr Asn Met Val Val Gly Glu Phe
        850                 855                 860
Gly Gly Leu Leu Asn Pro Ala Thr Gly Val Met Ile Pro Gly Phe Leu
865                 870                 875                 880
Gly Pro Ser Glu Gln Thr Gln Phe Ser Pro Glu Ile Glu Asp Gly Gly
                885                 890                 895
Ile Ile Pro Pro Glu Val Ala Ala Asn Ala Asp Lys Phe Lys Leu
                900                 905                 910
Ser Ile Pro Pro Ser Val Pro Glu Ser Ile Pro Glu Lys Asp Gln Lys
        915                 920                 925
Ile Asp Ser Ile Ser Glu Leu Met Tyr Asp Ile Glu Ser Gly Arg Leu
        930                 935                 940
Ile Gly Gln Val Ser Lys Arg Pro Ile Pro Gly Ser Ile Ala Gly Asp
945                 950                 955                 960
Leu Asn Pro Ile Met Lys Thr Pro Thr Gln Thr Asp Ser Val Thr Gly
                965                 970                 975
Lys Pro Ile Asp Pro Thr Thr Gly Leu Pro Phe Asn Pro Thr Gly
                980                 985                 990
His Leu Ile Asn Pro Thr Asn Asn Thr Met Asp Ser Ser Phe Ala
        995                 1000                1005
Gly Ala Tyr Lys Tyr Ala Val Ser Asn Gly Ile Lys Thr Asp Asn Val
        1010                1015                1020
Tyr Gly Leu Pro Val Gly Glu Ile Thr Gly Leu Pro Lys Asp Pro Gly
1025                1030                1035                1040
Ser Asp Ile Pro Phe Asn Ser Thr Thr Gly Glu Leu Val Asp Pro Ser
                1045                1050                1055
Thr Gly Lys Pro Ile Asn Asn Ser Thr Ala Gly Ile Val Ser Gly Lys
                1060                1065                1070
Pro Gly Leu Pro Pro Ile Glu Asp Glu Asn Gly Asn Leu Phe Asp Pro
        1075                1080                1085
Ser Thr Asn Leu Pro Ile Asp Gly Asn Asn Gln Leu Val Asn Pro Glu
        1090                1095                1100
Thr Asn Ser Thr Val Ser Gly Ser Thr Ser Gly Thr Thr Lys Pro Lys
1105                1110                1115                1120
Pro Gly Ile Pro Val Asn Gly Gly Val Pro Asp Glu Glu Ala
                1125                1130                1135
Lys Asp Gln Ala Asp Lys Gly Lys Asp Gly Leu Ile Val Pro Pro Thr
        1140                1145                1150
Asn Ser Ile Asn Lys Asp Pro Val Thr Asn Thr Gln Tyr Ser Asn Thr
        1155                1160                1165
Thr Gly Asn Ile Ile Asn Pro Glu Thr Gly Lys Val Ile Pro Gly Ser
        1170                1175                1180
```

-continued

Leu Pro Gly Ser Leu Asn Tyr Pro Ser Phe Asn Thr Pro Gln Gln Thr
1185                1190                1195                1200

Asp Glu Ile Thr Gly Lys Pro Val Asp Thr Val Thr Gly Leu Pro Tyr
            1205                1210                1215

Asp Pro Ser Thr Gly Glu Ile Ile Asp Pro Ala Thr Lys Leu Pro Ile
        1220                1225                1230

Pro Gly Ser Val Ala Gly Asp Glu Ile Leu Thr Glu Val Leu Asn Ile
    1235                1240                1245

Thr Thr Asp Glu Val Thr Gly Leu Pro Ile Asp Leu Glu Thr Gly Leu
1250                1255                1260

Pro Arg Asp Pro Val Ser Gly Leu Pro Gln Leu Pro Asn Gly Thr Leu
1265                1270                1275                1280

Val Asp Pro Ser Asn Lys Lys Pro Ile Pro Gly Ser His Ser Gly Phe
            1285                1290                1295

Ile Asn Gly Thr Ser Gly Glu Gln Ser His Glu Lys Asp Pro Ser Thr
        1300                1305                1310

Gly Lys Pro Leu Asp Pro Asn Thr Gly Leu His Pro Phe Asp Glu Asp
    1315                1320                1325

Ser Gly Ser Leu Ile Asn Pro Glu Thr Gly Asp Lys Leu Gln Gly Ser
1330                1335                1340

His Ser Gly Thr Phe Met Pro Val Pro Gly Lys Pro Gln Gly Glu Asn
1345                1350                1355                1360

Gly Gly Ile Met Thr Pro Glu Gln Ile Leu Glu Ala Leu Asn Lys Leu
            1365                1370                1375

Pro Thr Ser Asn Glu Val Asn Ile Ser Pro Arg Pro Ser Ser Asp Ala
        1380                1385                1390

Val Pro Asp Arg Pro Thr Asn Thr Trp Trp Asn Lys Ile Ser Gly Gln
    1395                1400                1405

Thr Tyr Gln Val Asp Gly Lys Lys Thr Ile Leu Gly Ser Ala Ala Ser
1410                1415                1420

Val Ile His Thr Ala Leu Gly Thr Pro Thr Gln Thr Asp Pro Thr Thr
1425                1430                1435                1440

Gly Leu Pro Ser Asp Pro Ser Thr Gly Leu Pro Phe Ile Pro Gly Phe
            1445                1450                1455

Asn Val Leu Val Asp Pro Gln Thr Gly Glu Gln Ile Lys Gly Ser Val
        1460                1465                1470

Pro Tyr Val Ser Leu Tyr Val Lys Glu Lys Asn Ile Val Thr Glu Ala
    1475                1480                1485

Ala Tyr Gly Leu Pro Val Asp Pro Lys Thr Gly Phe Pro Ile Asp Pro
1490                1495                1500

Ile Ser Tyr Leu Pro Phe Ala Lys Asn Gly Glu Leu Ile Asp Pro Ile
1505                1510                1515                1520

Ser Gly Lys Tyr Phe Ser Gly Ser Ile Ala Gly Phe Ile Ser Gly Lys
            1525                1530                1535

Ala Gly Ser Gln Ser Lys Ser Ser Asp Glu Ser Gly Asn Pro Ile Asp
        1540                1545                1550

Pro Ser Thr Asn Met Pro Tyr Asp Pro Lys Gly Gly Lys Leu Ile Asp
    1555                1560                1565

Pro Glu Ser Gly Ile Ala Ile Asp Asn Ser Val Ser Gly Val Phe Ala
1570                1575                1580

Thr Val Pro Gly Thr Ala Ala Pro Lys Lys Gly Gly Val Ile Pro Glu
1585                1590                1595                1600

Ser Val Ala Ala Glu Ala Ala Lys Lys Tyr Phe Ala Ala Asn Val Glu

-continued

```
                    1605                1610                1615

Gly Glu Gly Glu Gly Glu Val Pro Pro Pro Glu Ser Ser Ser
            1620                1625                1630

Asn Ile Ala Ile Gln Ala Ala Gly Gly Ala Ser Ala Ala Val Gly Leu
    1635                1640                1645

Val Ala Ala Val Gly Ala Trp Tyr Ala Ser Arg Asn Arg Gln Glu Gly
    1650                1655                1660

Glu Asp Asp Asp Tyr Gln Met Asp Leu Lys Gln Asn Met Lys Lys
1665                1670                1675                1680

Lys Arg Lys Lys Arg Val Met Lys Gln Gln Met Lys Leu Leu Leu Gln
                1685                1690                1695

Leu Ser Val Ile His His Ser Gly Thr Asn Leu Lys Arg Arg Lys Asp
            1700                1705                1710

Phe Ser Asn Ser Lys Lys Phe Arg Ile
        1715                1720

<210> SEQ ID NO 6
<211> LENGTH: 503
<212> TYPE: PRT
<213> ORGANISM: Cryptosporidium parvum

<400> SEQUENCE: 6

Ser Lys Gly Gln Leu Phe Asn Pro Val Ser Lys Leu Cys Val Arg Leu
1               5                   10                  15

Lys Asp Asn Val Val Gly Gly Ala Leu Val Leu Asp Asp Cys Arg
            20                  25                  30

Lys Ala Ser Asp Gly Ser Gly Leu Phe Glu Leu Met Pro Asn Asn Gln
        35                  40                  45

Leu Arg Leu Ala Arg Gly Gly Asn Leu Cys Leu Thr Ser Pro Gly Asp
    50                  55                  60

Lys Pro Gly Val Ala Asn Val Ala Leu Asn Ser Ala Ala Ser Ser Thr
65                  70                  75                  80

Ser Val Val Arg Thr Gly Ile Glu Asn Gly Pro Ala Met Ala Val Asp
                85                  90                  95

Gly Lys Asp Thr Ser Tyr Trp Leu Ser Asp Ser Ser Thr Pro Gly Lys
            100                 105                 110

Asp Ser Ala Asn Val Asn Phe Leu Ser Asp Thr Gly Ser Val Thr Lys
        115                 120                 125

Leu Lys Asp Ile Phe Ile Glu Trp Lys Tyr Pro Ala Ile Asp Phe Asn
    130                 135                 140

Ile Asp Leu Ser Glu Asn Gly Lys Glu Tyr Gln Thr Gln Val Ser Val
145                 150                 155                 160

Asn Asn Asn Gly Leu Met Ser Thr Thr Tyr Ser Leu Glu Gly Lys Lys
                165                 170                 175

Ala Arg Tyr Val Lys Ile Gln Met Thr Ile Pro Ser Gln Asp Glu Thr
            180                 185                 190

Gly Lys Tyr Val Tyr Gly Ile Lys Gln Val Arg Ile Phe Ser Asn Thr
        195                 200                 205

Met Arg Ser Thr Val Glu Asp Cys Ser Ser Val Lys Gln His Asn Asp
    210                 215                 220

Gly Arg Asp Lys Ile Phe Pro Leu Pro Tyr Asn Gly Asp Asn Phe Ala
225                 230                 235                 240

Pro Gly Leu Leu Leu Lys Ala His Gly Ile Ser Val Lys Asn Arg Leu
                245                 250                 255

Asn Glu Leu Gln Glu Leu Ser Gly Lys Val Thr Ser Ile Leu Pro Asn
```

```
                    260                 265                 270
Leu Asp Ala Cys Arg Lys Thr Ser Asp Gly Arg Asp Asn Thr Leu Lys
            275                 280                 285

Met Gln Ala Thr Lys Leu Gly Phe Leu Ser Glu Lys Leu Glu Lys Leu
    290                 295                 300

Thr Ser Asp Tyr Asn Leu Glu Tyr Lys Phe Thr Lys Pro Ala Leu Gly
305                 310                 315                 320

Gly Ser Glu Leu Tyr Pro Gly Glu Asp Cys Val Ala Ile Lys Asn Asp
                325                 330                 335

Lys Thr Gln Glu Ala Ile Ser Gly Phe Tyr Tyr Val Arg Pro Phe Cys
            340                 345                 350

Ser Thr Lys Pro Leu Arg Val Tyr Cys Asp Met Asn Thr Gly Asn Thr
        355                 360                 365

Ile Tyr Pro Met Glu Met Ser Val His Ser Ser Arg Ala Ala Ser Ser
    370                 375                 380

Ala Cys Ala Thr Val Gly Leu Lys Pro Leu Leu Arg Asp Lys Lys
385                 390                 395                 400

Glu Ser Val Val Gly Ile Lys Lys Met Leu Asn Met Met Asn Ile Asn
                405                 410                 415

Asp Asn Arg Arg Val Ile Pro Leu Thr His Asp Phe Gly Cys Asp Asn
            420                 425                 430

Pro Lys Gly Cys Asn Ser Gln Phe Thr Gln Leu Gly Ser Gly Val Glu
        435                 440                 445

Glu Phe Val Ala Ala Ser Pro Gln Ala Ala Ser Asn Ser Thr Ser
    450                 455                 460

Gly Ala Leu Pro Glu Leu Val Leu Cys Ser Thr Asn Thr Asn Leu Lys
465                 470                 475                 480

His Glu Ser Asn Ala Ile Ser Leu Ser Cys Glu Ser Arg Phe Ser Asp
                485                 490                 495

Met Lys Val Phe His Leu Asp
            500

<210> SEQ ID NO 7
<211> LENGTH: 128
<212> TYPE: PRT
<213> ORGANISM: Cryptosporidium parvum
<220> FEATURE:
<223> OTHER INFORMATION: mutant/variant of SEQ ID NO:5

<400> SEQUENCE: 7

Met Gly Ser Lys Val Tyr Ile Pro Tyr Thr Lys Cys Val Gly Val Lys
1               5                   10                  15

His Thr Thr Thr Thr Thr Thr Thr Thr Thr Thr Thr Thr Thr Thr Thr
                20                  25                  30

Thr Thr Thr Thr Thr Thr Thr Thr Thr Thr Thr Thr Thr Thr Thr Thr
            35                  40                  45

Thr Thr Thr Thr Thr Thr Thr Thr Thr Thr Thr Thr Thr Thr Thr Thr
        50                  55                  60

Thr Thr Thr Thr Thr Thr Thr Thr Thr Thr Thr Thr Thr Thr Thr Thr
65                  70                  75                  80

Thr Thr Lys Lys Pro Thr Thr Thr Thr Thr Thr Thr Thr Thr Thr Thr
                85                  90                  95

Thr Lys Lys Pro Thr Thr Thr Thr Ala Thr Thr Thr Thr Thr Thr Thr
            100                 105                 110

Ser Glu Thr Glu Ser Val Ile Lys Pro Asp Glu Trp Cys Trp Leu Glu
        115                 120                 125
```

<210> SEQ ID NO 8
<211> LENGTH: 130
<212> TYPE: PRT
<213> ORGANISM: Cryptosporidium parvum
<220> FEATURE:
<223> OTHER INFORMATION: mutant/variant of SEQ ID NO:5

<400> SEQUENCE: 8

Met Gly Ser Lys Val Tyr Ile Pro Tyr Thr Lys Cys Val Gly Val Lys
1               5                   10                  15

His Thr Thr Thr Thr Thr Thr Thr Thr Thr Thr Thr Thr Thr Thr Thr
            20                  25                  30

Thr Thr Thr Thr Thr Thr Thr Thr Thr Thr Thr Thr Thr Thr Thr Thr
        35                  40                  45

Thr Thr Thr Thr Thr Thr Thr Thr Thr Thr Thr Thr Thr Thr Thr Thr
    50                  55                  60

Thr Thr Thr Thr Thr Thr Thr Thr Thr Thr Thr Thr Thr Thr Thr Thr
65                  70                  75                  80

Thr Thr Thr Thr Lys Lys Pro Thr Thr Thr Thr Thr Thr Thr Thr Thr
                85                  90                  95

Thr Thr Thr Lys Lys Pro Thr Thr Thr Thr Thr Ala Thr Thr Thr Thr
            100                 105                 110

Thr Thr Ser Glu Thr Glu Ser Val Ile Lys Pro Asp Glu Trp Cys Trp
        115                 120                 125

Leu Glu
    130

<210> SEQ ID NO 9
<211> LENGTH: 130
<212> TYPE: PRT
<213> ORGANISM: Cryptosporidium parvum
<220> FEATURE:
<223> OTHER INFORMATION: mutant/variant of SEQ ID NO:5

<400> SEQUENCE: 9

Met Gly Ser Lys Val Tyr Ile Pro Tyr Thr Lys Cys Val Gly Val Lys
1               5                   10                  15

His Thr Thr Thr Thr Thr Thr Thr Thr Thr Thr Thr Thr Thr Thr Thr
            20                  25                  30

Thr Thr Thr Thr Thr Thr Thr Thr Thr Thr Thr Thr Thr Thr Lys Pro
        35                  40                  45

Thr Thr Thr Thr Thr Thr Thr Thr Thr Thr Thr Thr Thr Thr Thr Thr
    50                  55                  60

Thr Thr Thr Thr Thr Thr Thr Thr Thr Thr Thr Thr Thr Thr Thr Thr
65                  70                  75                  80

Thr Thr Thr Thr Lys Lys Pro Thr Thr Thr Thr Thr Thr Thr Thr Thr
                85                  90                  95

Thr Thr Thr Lys Lys Pro Thr Thr Thr Thr Thr Ala Thr Thr Thr Thr
            100                 105                 110

Thr Thr Ser Glu Thr Glu Ser Val Ile Lys Pro Asp Glu Trp Cys Trp
        115                 120                 125

Leu Glu
    130

<210> SEQ ID NO 10
<211> LENGTH: 138
<212> TYPE: PRT
<213> ORGANISM: Cryptosporidium parvum -continued

```
<220> FEATURE:
<223> OTHER INFORMATION: mutant/variant of SEQ ID NO:5

<400> SEQUENCE: 10

Met Gly Ser Lys Val Tyr Ile Pro Tyr Thr Lys Cys Val Gly Val Lys
  1               5                  10                  15

His Thr Thr Thr Thr Thr Thr Thr Thr Thr Thr Thr Thr Thr Thr Thr
                 20                  25                  30

Thr Thr Thr Thr Thr Thr Thr Thr Thr Thr Thr Thr Thr Thr Thr Thr
             35                  40                  45

Thr Thr Thr Thr Thr Thr Thr Thr Thr Thr Thr Thr Thr Thr Thr Thr
         50                  55                  60

Thr Thr Thr Thr Thr Thr Thr Thr Thr Thr Thr Thr Thr Thr Thr Thr
 65                  70                  75                  80

Thr Thr Thr Thr Thr Thr Thr Thr Thr Thr Thr Lys Lys Pro Thr
                 85                  90                  95

Thr Thr Thr Thr Thr Thr Thr Thr Thr Lys Lys Pro Thr Thr
                100                 105                 110

Thr Thr Thr Ala Thr Thr Thr Thr Thr Thr Ser Glu Thr Glu Ser Val
            115                 120                 125

Ile Lys Pro Asp Glu Trp Cys Trp Leu Glu
        130                 135

<210> SEQ ID NO 11
<211> LENGTH: 124
<212> TYPE: PRT
<213> ORGANISM: Cryptosporidium parvum
<220> FEATURE:
<223> OTHER INFORMATION: mutant/variant of SEQ ID NO:5

<400> SEQUENCE: 11

Met Gly Ser Lys Val Tyr Ile Pro Tyr Thr Lys Cys Val Gly Val Lys
  1               5                  10                  15

His Thr Thr Thr Thr Thr Thr Thr Thr Thr Thr Thr Thr Thr Thr Thr
                 20                  25                  30

Thr Thr Thr Thr Thr Thr Thr Thr Thr Thr Thr Thr Thr Thr Thr Thr
             35                  40                  45

Thr Thr Thr Thr Thr Thr Thr Thr Thr Thr Thr Thr Thr Thr Thr Thr
         50                  55                  60

Thr Thr Thr Thr Thr Thr Thr Thr Thr Thr Thr Thr Thr Thr Lys Glu
 65                  70                  75                  80

Pro Thr Thr Thr Thr Thr Thr Thr Thr Thr Thr Thr Lys Lys Pro
                 85                  90                  95

Thr Thr Thr Thr Thr Ala Thr Thr Thr Thr Thr Thr Ser Glu Thr Glu
                100                 105                 110

Ser Val Ile Lys Pro Asp Glu Trp Cys Trp Leu Glu
            115                 120

<210> SEQ ID NO 12
<211> LENGTH: 175
<212> TYPE: PRT
<213> ORGANISM: Cryptosporidium parvum
<220> FEATURE:
<223> OTHER INFORMATION: mutant/variant of SEQ ID NO:5

<400> SEQUENCE: 12

Met Gly Ser Lys Val Tyr Ile Pro Tyr Thr Lys Cys Val Gly Val Lys
  1               5                  10                  15

His Thr Thr Thr Thr Thr Thr Thr Thr Thr Thr Thr Thr Thr Thr Thr
```

```
                     20                  25                  30

Thr Thr Thr Thr Thr Thr Thr Thr Thr Thr Thr Thr Thr Thr Thr
                 35                  40                  45

Thr Thr Thr Thr Thr Thr Thr Thr Thr Thr Thr Thr Thr Thr Thr
             50                  55                  60

Thr Thr Thr Thr Thr Thr Thr Thr Thr Thr Thr Thr Thr Thr Thr
 65                  70                  75                  80

Thr Thr Thr Thr Lys Lys Pro Thr Thr Thr Thr Thr Thr Thr Thr
                 85                  90                  95

Thr Thr Thr Thr Thr Thr Thr Thr Thr Thr Thr Thr Thr Thr Thr
            100                 105                 110

Thr Thr Thr Thr Thr Thr Thr Thr Thr Thr Thr Thr Thr Thr Thr
            115                 120                 125

Thr Lys Lys Pro Thr Thr Thr Thr Thr Thr Thr Thr Thr Thr Thr
        130                 135                 140

Lys Lys Pro Thr Thr Thr Thr Ala Thr Thr Thr Thr Thr Thr Ser
145                 150                 155                 160

Glu Thr Glu Ser Val Ile Lys Pro Asp Glu Trp Cys Trp Leu Glu
                165                 170                 175

<210> SEQ ID NO 13
<211> LENGTH: 162
<212> TYPE: PRT
<213> ORGANISM: Cryptosporidium parvum
<220> FEATURE:
<223> OTHER INFORMATION: mutant/variant of SEQ ID NO:5

<400> SEQUENCE: 13

Val Ala Arg Met Gly Ser Lys Val Tyr Ile Pro Tyr Thr Lys Cys Val
 1               5                  10                  15

Gly Val Lys His Thr Thr Thr Thr Thr Thr Thr Thr Thr Thr Thr
                 20                  25                  30

Thr Thr Thr Thr Thr Thr Thr Thr Thr Thr Thr Thr Thr Thr Thr
                 35                  40                  45

Thr Thr Thr Thr Thr Val Ala Arg Thr Thr Thr Thr Thr Thr Thr
             50                  55                  60

Thr Thr Ala Thr Thr Thr Thr Thr Val Ala Arg Thr Thr Thr Thr
 65                  70                  75                  80

Thr Thr Thr Thr Thr Thr Thr Thr Thr Thr Thr Thr Thr Thr Thr
                 85                  90                  95

Thr Thr Thr Thr Thr Thr Thr Thr Thr Thr Thr Thr Thr Val Ala
            100                 105                 110

Arg Thr Thr Thr Lys Lys Pro Thr Thr Thr Thr Thr Thr Thr Thr
        115                 120                 125

Thr Thr Thr Lys Lys Pro Thr Thr Thr Thr Ala Thr Thr Thr Thr
        130                 135                 140

Thr Thr Ser Glu Thr Glu Ser Val Ile Lys Pro Asp Glu Trp Cys Trp
145                 150                 155                 160

Leu Glu

<210> SEQ ID NO 14
<211> LENGTH: 91
<212> TYPE: PRT
<213> ORGANISM: Cryptosporidium parvum
<220> FEATURE:
<223> OTHER INFORMATION: mutant/variant of SEQ ID NO:5

<400> SEQUENCE: 14
```

```
Met Gly Ser Lys Val Tyr Ile Pro Tyr Thr Lys Cys Val Gly Val Lys
 1               5                  10                  15

His Thr Thr Thr Thr Thr Thr Thr Thr Thr Thr Thr Thr Thr Thr
             20                  25                  30

Thr Thr Thr Thr Thr Thr Thr Thr Thr Thr Thr Thr Thr Thr
         35                  40                  45

Thr Thr Thr Thr Thr Thr Thr Thr Thr Thr Thr Lys Lys Pro Thr
     50                  55                  60

Thr Thr Thr Thr Ala Thr Thr Thr Thr Thr Thr Ser Glu Thr Glu Ser
 65                  70                  75                  80

Val Ile Lys Pro Asp Glu Trp Cys Trp Leu Glu
                 85                  90
```

<210> SEQ ID NO 15
<211> LENGTH: 249
<212> TYPE: PRT
<213> ORGANISM: Cryptosporidium parvum
<220> FEATURE:
<223> OTHER INFORMATION: mutant/variant of SEQ ID NO:5

<400> SEQUENCE: 15

```
Met Gly Ser Lys Val Tyr Ile Pro Tyr Thr Lys Cys Val Gly Val Lys
 1               5                  10                  15

His Thr Thr Thr Thr Thr Thr Thr Thr Thr Thr Thr Thr Thr Thr
             20                  25                  30

Thr Thr Thr Thr Thr Thr Thr Thr Thr Thr Thr Thr Thr Thr
         35                  40                  45

Thr Thr Thr Thr Thr Thr Thr Thr Thr Thr Thr Thr Thr Thr
     50                  55                  60

Thr Thr Thr Thr Thr Thr Thr Thr Thr Thr Thr Thr Thr Thr Thr Thr
 65                  70                  75                  80

Thr Thr Thr Thr Thr Thr Thr Thr Thr Thr Thr Thr Thr Thr Thr
                 85                  90                  95

Thr Thr Thr Thr Thr Thr Thr Thr Thr Thr Thr Thr Thr Thr Thr
             100                 105                 110

Thr Thr Thr Thr Thr Thr Thr Thr Thr Thr Thr Thr Thr Thr Thr
         115                 120                 125

Thr Thr Thr Thr Thr Thr Thr Thr Thr Thr Thr Thr Thr Thr Thr
     130                 135                 140

Thr Thr Thr Thr Thr Thr Thr Thr Thr Thr Thr Thr Thr Thr Thr Thr
145                 150                 155                 160

Thr Thr Lys Lys Pro Thr Thr Thr Thr Thr Thr Thr Thr Thr Thr
             165                 170                 175

Thr Thr Thr Thr Thr Thr Thr Thr Thr Thr Thr Thr Thr Thr Thr
         180                 185                 190

Thr Thr Thr Thr Thr Thr Thr Thr Thr Thr Lys Pro Thr Thr
     195                 200                 205

Thr Thr Thr Thr Thr Thr Thr Thr Thr Lys Lys Pro Thr Thr Thr
     210                 215                 220

Thr Thr Ala Thr Thr Thr Thr Thr Thr Ser Glu Thr Glu Ser Val Ile
225                 230                 235                 240

Lys Pro Asp Glu Trp Cys Trp Leu Glu
                 245
```

What is claimed is:

1. An isolated and sequenced Cryptosporidium antigen GP900 detected at the surface of Cryptosporidium sporozoites or merozoites comprising 1721 amino acid sequence SEQ ID NO: 5,
   wherein said antigen has a molecular weight greater than 900 kilodaltons,
   wherein said antigen is detected by anti-GP900 antibodies raised against said antigen amino acid sequence SEQ ID NO: 5, and
   wherein said anti-GP900 antibodies structurally interact with the GP900 antigen and inhibit Cryptosporidium infection, invasion or adhesion.

2. The antigen of claim 1 comprising glycoprotein attached thereto.

3. The antigen of claim 1 detected with the polyclonal GP900 antibodies.

4. The antigen of claim 1 wherein the polyclonal anti-GP900 antibodies are obtained by animal immunization.

5. The antigen of claim 1 detected with the monoclonal anti-GP900 antibodies.

6. The antigen of claim 5 detected with the monoclonal anti-GP900 antibodies obtained by animal immunization with a supernatant from sonicated *Cryptosporidium parvum* ocysts.

7. The antigen of claim 6 wherein the monoclonal anti-GP900 antibodies detecting said antigen are 10C6, 7B3, E6, M2, M10, M15 or M24.

8. An isolated and sequenced Cryptosporidium antigen P68 which is an apical protein of Cryptosporidium sporozoites or merozoites comprising 503 amino acid sequence SEQ ID NO: 6,
   wherein said antigen has a molecular weight between 50 and 100 kilodaltons,
   wherein said antigen is detected by anti-P68 antibodies raised against said antigen amino acid sequence SEQ ID NO: 6; and
   wherein said anti-P68 antibodies structurally interact with the P68 antigen and inhibit Cryptosporidium sporozoites or merozoites infection, invasion or adhesion.

9. The antigen of claim 8 detected with the polyclonal or monoclonal anti-P68 antibodies.

10. The antigen of claim 9 detected with the monoclonal anti-P68 antibodies.

11. The antigen of claim 10 detected with the polyclonal anti-P68 antibodies obtained by animal immunization.

12. A purified recombinant Cryptosporidium GP900 antigen protein comprising 1721 amino acid sequence SEQ ID NO: 5, or a variant or mutant thereof;
   wherein said protein has a molecular weight greater than 900 kilodaltons;
   wherein said protein is detected with a specific anti-GP900 antibodies raised against a protein comprising amino acid sequence SEQ ID NO: 5;
   wherein said protein comprises four domains wherein domains 1 and 3 are cysteine rich domains and wherein domains 2 and 4 are mucin like domains containing threonines; and
   wherein mutation or variation occurs within amino acids 175–423 of the sequence SEQ ID NO: 5; and
   wherein the mutant or variant is selected from the group consisting of amino acid sequences identified as SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14 and SEQ ID NO: 15.

13. The protein of claim 12 encoded by the cDNA sequence identified as SEQ ID NO: 1.

14. The protein of claim 12 encoded by the cDNA sequence identified as SEQ ID NO: 2.

15. The protein of claim 12 containing a covalently N-linked, O-linked or N-linked and O-linked carbohydrate.

16. The protein of claim 12 deglycosylated.

17. The protein of claim 16 wherein the deglycosylated protein has a molecular weight between 150 and 180 kilodaltons.

* * * * *